United States Patent
Rokhsar

(10) Patent No.: US 12,012,594 B2
(45) Date of Patent: *Jun. 18, 2024

(54) METHODS AND COMPOSITIONS FOR LONG-RANGE HAPLOTYPE PHASING

(71) Applicant: The Regents of the University of California, Oakland, CA (US)

(72) Inventor: Daniel S. Rokhsar, Kensington, CA (US)

(73) Assignee: The Regents of the University of California, Oakland, CA (US)

( * ) Notice: Subject to any disclaimer, the term of this patent is extended or adjusted under 35 U.S.C. 154(b) by 86 days.

This patent is subject to a terminal disclaimer.

(21) Appl. No.: 17/721,195

(22) Filed: Apr. 14, 2022

(65) Prior Publication Data
US 2023/0074770 A1 Mar. 9, 2023

Related U.S. Application Data

(63) Continuation of application No. 15/564,384, filed as application No. PCT/US2016/025901 on Apr. 4, 2016, now Pat. No. 11,326,159.

(60) Provisional application No. 62/278,761, filed on Jan. 14, 2016, provisional application No. 62/143,730, filed on Apr. 6, 2015.

(51) Int. Cl.
| | |
|---|---|
| C40B 40/06 | (2006.01) |
| B01J 19/00 | (2006.01) |
| C12N 15/10 | (2006.01) |
| C12P 19/34 | (2006.01) |
| C12Q 1/6869 | (2018.01) |
| C40B 50/00 | (2006.01) |
| G16B 50/00 | (2019.01) |
| G16B 50/30 | (2019.01) |

(52) U.S. Cl.
CPC ...... *C12N 15/1065* (2013.01); *B01J 19/0046* (2013.01); *C12N 15/1006* (2013.01); *C12P 19/34* (2013.01); *C12Q 1/6869* (2013.01); *C40B 40/06* (2013.01); *C40B 50/00* (2013.01); *G16B 50/00* (2019.02); *G16B 50/30* (2019.02); *C12Q 2525/191* (2013.01); *C12Q 2563/185* (2013.01)

(58) Field of Classification Search
None
See application file for complete search history.

(56) References Cited

U.S. PATENT DOCUMENTS

| | | | |
|---|---|---|---|
| 11,326,159 B2 * | 5/2022 | Rokhsar | B01J 19/0046 |
| 2005/0158765 A1 | 7/2005 | Morgan et al. | |
| 2009/0246780 A1 | 10/2009 | Van Eijk et al. | |
| 2012/0245037 A1 | 9/2012 | Hogers et al. | |
| 2013/0096009 A1 | 4/2013 | Dekker et al. | |
| 2013/0196331 A1 | 8/2013 | Miyamoto et al. | |
| 2013/0203605 A1 * | 8/2013 | Shendure | C12N 15/1093 506/2 |
| 2014/0220587 A1 | 8/2014 | Green et al. | |
| 2016/0312213 A1 | 10/2016 | Rokhsar et al. | |
| 2017/0335369 A1 | 11/2017 | Fields et al. | |

FOREIGN PATENT DOCUMENTS

WO  WO 2014121091  8/2014

OTHER PUBLICATIONS

Adey et al. (2010) "Rapid, low-input, low-bias construction of shotgun fragment libraries by high-density in vitro transposition" Genome Biology, 11: R119, 17 pages.

Illumina (Illumina Adapter Sequences brochure; 53 pages; downloaded from the internet Jan. 20, 2021 (Year: 2020).

* cited by examiner

*Primary Examiner* — Christopher M Gross
(74) *Attorney, Agent, or Firm* — Brian E. Davy; Bozicevic, Field & Francis LLP

(57) ABSTRACT

Various approaches for generating read-sets from nucleic acid molecules and segments and phasing are disclosed. Nucleic acids are assembled into complexes using binding moieties and exposed nucleic acid ends are tagged with nucleic acid tags. Read-sets can be generated from tagged nucleic acid molecules and segments. Physical linkage relationships between nucleic acid molecules and segments can be examined using the nucleic acid tags. Various approaches to generating read-sets and phasing are presented.

20 Claims, 4 Drawing Sheets

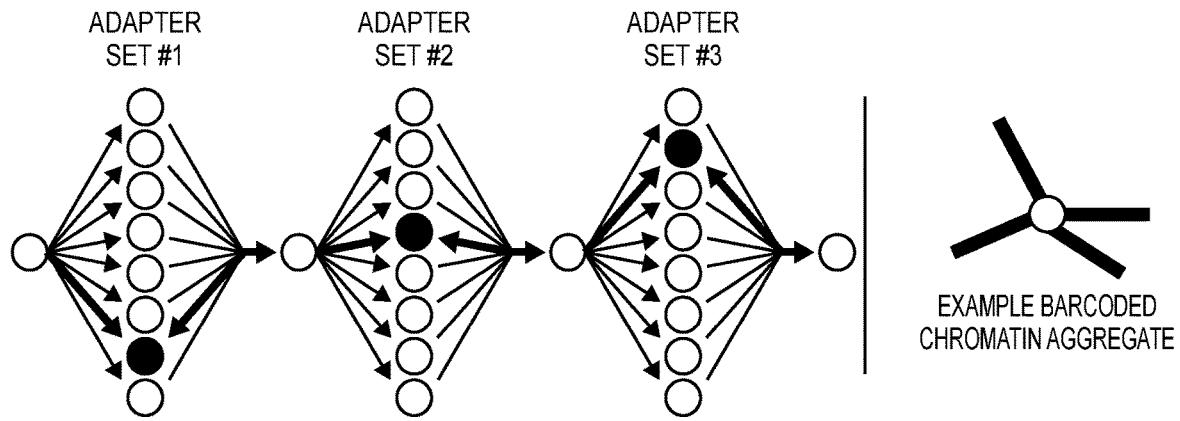
FIG. 1A
FIG. 1B
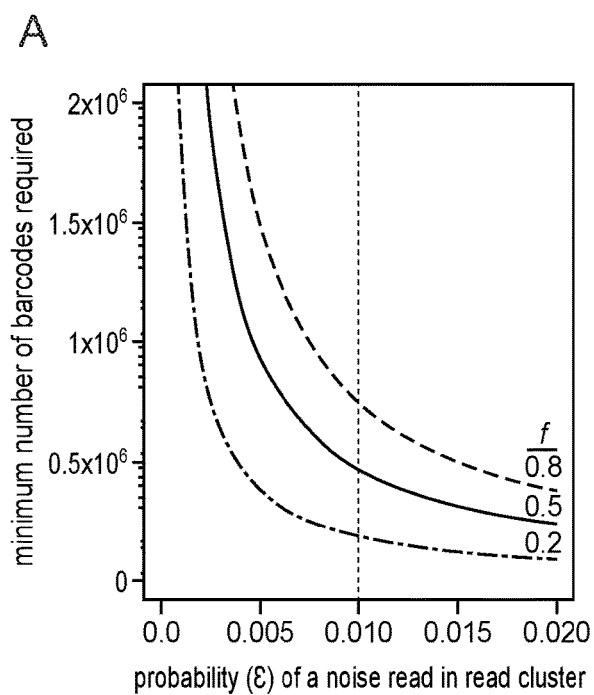
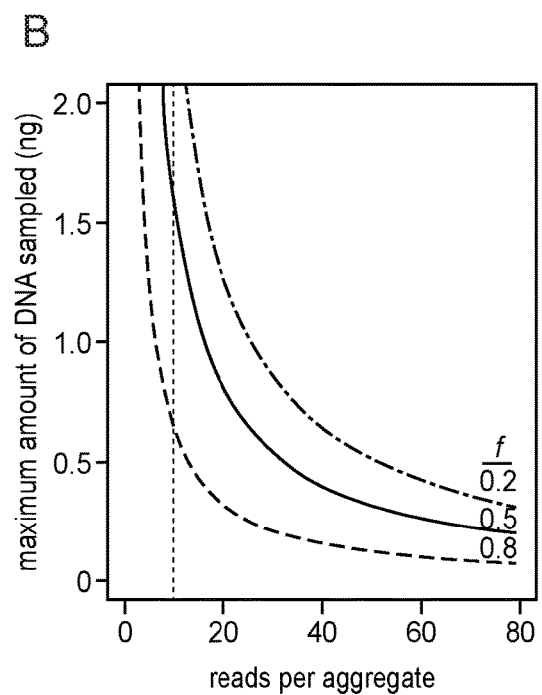
FIG. 2A
FIG. 2B

METHODS AND COMPOSITIONS FOR LONG-RANGE HAPLOTYPE PHASING

CROSS-REFERENCE TO RELATED APPLICATIONS

This application claims priority to provisional patent application Ser. No. 62/278,761, filed Jan. 14, 2016 and to provisional application Ser. No. 62/143,730 filed Apr. 6, 2015, both of which are hereby incorporated by reference in their entirety.

STATEMENT OF GOVERNMENTAL SUPPORT

None.

REFERENCE TO SEQUENCE LISTING, COMPUTER PROGRAM, OR COMPACT DISK

None.

BACKGROUND

Existing sequencing technologies can generate large data sets comprising sequencing reads. Accurate analysis of sequence variation requires methods for haplotype phasing. Generally, these technologies produce vast amounts of data, but only for short stretches of nucleic acid sequences. Placing these short stretches of sequence relative to one another is challenging, particularly if the sequence includes repetitive regions or is from a heterozygous diploid or polyploid organism. The present disclosure provides methods and compositions which can be used for generating read-sets and for long-range haplotype phasing.

BRIEF SUMMARY OF THE INVENTION

Methods of generating sequence reads that contain information relevant to phasing are disclosed. In some cases, a method of generating a first read-set from a first nucleic acid molecule comprises: (a) binding the first nucleic acid molecule outside of a cell and thereby generating a first complex, wherein the first nucleic acid molecule comprises a first nucleic acid segment and a second nucleic acid segment; (b) labeling each of the first nucleic acid segment and the second nucleic acid segment using a first barcode nucleic acid; (c) labeling each of the first nucleic acid segment and the second nucleic acid segment using a second barcode nucleic acid; and (d) sequencing the first labeled nucleic acid segment and the second labeled nucleic acid segment, thereby obtaining the first read-set. The first barcode nucleic acid is hybridized to the first nucleic acid segment and the second nucleic acid segment, or alternately the first barcode nucleic acid is ligated to the first nucleic acid segment and the second nucleic acid segment. Similarly, the second barcode nucleic acid is hybridized to the first barcode nucleic acid, or alternately, the second barcode nucleic acid is ligated to the first barcode nucleic acid. In some cases, binding the first nucleic acid molecule outside of a cell comprises cross-linking. A first plurality of association molecules is bound to the first nucleic acid molecule. In some cases the association molecules are covalently bound, for example by cross-linking. In some cases the association molecules are non-covalently bound to nucleic acids, for example by the activity of a nucleic acid binding protein. In many cases, the association molecules comprise amino acids, such as amino acids bound into polypeptide beads. Alternately, some association molecules are nanoparticles rather than polypeptides, and comprise little or no polypeptide bonds. In some cases, the first nucleic acid molecule comprises DNA. In some cases, the first barcode nucleic acid comprises DNA. In some cases, the first nucleic acid molecule is cross-linked to an association molecule using a cross-linking agent or fixative agent such as formaldehyde, psoralen, or UV light. In some cases, the fixative agent comprises formaldehyde. In some cases, the first complex is treated such that the first nucleic acid segment and the second nucleic acid segment are not joined by a phosphodiester bond. In some cases, the first barcode nucleic acid and the second barcode nucleic acid are non-identical. In some cases, the method comprises labeling the first nucleic acid segment and the second nucleic acid segment using at least a third barcode nucleic acid. In some cases, the third barcode nucleic acid is non-identical to the first barcode nucleic acid and the second barcode nucleic acid. In some cases, the first read-set is generated by associating the first nucleic acid segment and the second nucleic acid segment using the first barcode nucleic acid and the second barcode nucleic acid. In some cases, the method comprises assembling a first contig having the first nucleic acid segment and a second contig having the second nucleic acid segment into a single scaffold. In some cases, the method comprises assigning the first nucleic acid segment and the second nucleic acid segment to a common phase. In some cases, the method comprises assigning a first sequence read having the first barcode nucleic acid and the second barcode nucleic acid to a common scaffold. In some cases, the method comprises assigning a first sequence read having the first barcode nucleic acid and the second barcode nucleic acid to a common phase. In some cases, the first nucleic acid molecule comprises a third nucleic acid segment labeled with the first barcode nucleic acid and the second barcode nucleic acid. The third nucleic acid segment is sequenced in some cases, and the first read-set comprises a sequence of the third nucleic acid segment.

In some cases, the method comprises: (a) binding, such as crosslinking, a second plurality of association molecules to a second nucleic acid molecule outside of a cell, thereby forming a second complex; (b) severing the second complex, thereby generating a third nucleic acid segment and a fourth nucleic acid segment; (c) labeling each of the third nucleic acid segment and the fourth nucleic acid segment with the first barcode nucleic acid; (d) separating the first nucleic acid molecule from the second nucleic acid molecule; (e) labeling each of the third nucleic acid segment and the fourth nucleic acid segment with a third barcode nucleic acid; and (f) sequencing the second linked nucleic acid segment and thereby obtaining a second read-set. In some cases, the method comprises assembling a plurality of contigs of the second nucleic acid molecule using the second read-set. In some cases, the first read-set and the second read-set are used to determine the phase of the first nucleic acid molecule and the second nucleic acid molecule.

Also disclosed herein are in vitro libraries. In some cases, an in vitro library comprises a plurality of read-sets each comprising at least a first nucleic acid segment and a second nucleic acid segment, wherein the first nucleic acid segment and the second nucleic acid segment are bound to a first barcode nucleic acid, and wherein each of the first barcode nucleic acid is bound to a second barcode nucleic acid. In some cases, each of the second barcode nucleic acid is bound to at least one additional barcode nucleic acid. In some cases, the first nucleic acid segment and the second nucleic acid segment each originate from a first nucleic acid molecule. In some cases, at least 1% of the read-sets comprise a first nucleic acid segment and a second nucleic acid segment that are at least 50 kB apart on the single nucleic acid molecule. In some cases, at least 10% of the read-pairs comprise a first nucleic acid segment and a second nucleic acid segment that are at least 50 kB apart on the first nucleic acid molecule. In some cases, at least 1% of the read-pairs comprise a first nucleic acid segment and a second nucleic acid segment that are at least 100 kB apart on the first nucleic acid molecule.

Also disclosed herein are compositions for nucleic acid sequence assembly. In some cases, a composition comprises a first nucleic acid segment and a second nucleic acid segment. In some cases, each of the first nucleic acid segment and a second nucleic acid segment are bound, such as by cross-linking, to a plurality of association molecules to thereby generate an in vitro complex, wherein each of the first nucleic acid segment and a second nucleic acid segment are attached, such as by hybridization, ligation or other covalent attachment, to a first barcode nucleic acid, and wherein each of the first barcode nucleic acid is attached, such as by hybridization, ligation or other covalent attachment, to a second barcode nucleic acid. In some cases, the in vitro complex is immobilized on a solid support, such as a magnetic bead. In some cases, each of the second barcode nucleic acid is attached, such as by hybridization, ligation, or other covalent attachment, to a third barcode nucleic acid.

Also disclosed herein are methods of assembling a plurality sequence reads into contigs or scaffolds. In some cases methods of assembling a plurality of contigs generated from a first nucleic acid molecule comprises (a) binding, such as by cross-linking, a plurality of nucleic acid molecules to a plurality of association molecules to form a plurality of complexes, wherein the plurality of nucleic acid molecules comprises the first nucleic molecule; (b) severing the nucleic acid molecules to generate a plurality of nucleic acid segments; (c) labeling nucleic acid segments via an iterative process; (d) sequencing the labeled nucleic acid segments and thereby generating a read-set; and (e) assembling the contigs using the read-pairs.

In some cases, the iterative process comprises: (i) attaching, such as by hybridization, ligation or other covalent attachment, a barcode nucleic acid to the nucleic acid segments; (ii) separating the first complex from a plurality of other complexes; and (iii) repeating steps (i) and (ii) at least one more time. An iterative process for labeling nucleic acid segments comprises at least one round of label or tag attachment. In an iterative process, complexes are divided into distinct volumes, wherein each volume contains tags having a sequence identical to all other tags in the same volume but having a sequence non-identical to tags of other volumes. The tags are attached, for example by hybridization, ligation or other covalent attachment. After the attachment of a first tag in a first iteration, tag attachment is repeated. The complexes in distinct volumes are pooled together and processed, for example through washing to remove previously used reagents and tags. The complexes are divided again into distinct volumes and attached to a second set of tags. The tags of the first set can be non-identical to the tags of the second set. In going through iterations of tag attachment, complexes are randomly distributed into distinct volumes. Due to random distribution, one complex can receive a tag pattern that is different form another complex depending on the number of distinct volumes per iteration and the number of iterations used.

Also disclosed herein are methods of phasing a plurality of contigs. In some cases, a method of phasing a plurality of contigs generated from a first nucleic acid molecule comprises: (a) binding, such as by cross-linking, a plurality of nucleic acid molecules to a plurality of association molecules to form a plurality of complexes, wherein the plurality of nucleic acid molecules comprises the first nucleic acid molecule; (b) severing the nucleic acid molecules to generate a plurality of nucleic acid segments; (c) labeling each of the nucleic acid segments via an iterative process; (d) sequencing the labeled nucleic acid segments and thereby generating a read-set; and (e) determining the contigs that originate from the first nucleic acid molecule using the read-set and thereby phasing the first nucleic molecule. Contigs can be determined by comparing sequencing reads to identify overlapping sequences, such as overlapping tag sequences or overlapping nucleic acid segment sequences. In some cases, sequence reads are compared against databases of known sequences in order to identify which sequencing reads have a high probability of being contiguous. However, not all sequencing reads with overlapping nucleic acid segments may be contiguous. A sequence read may comprise repetitive regions comprising sequence information that does not uniquely map to any single contig. Similarly, sequencing reads having overlapping tag patterns or common tag patterns may not map to a contig if the non-tag sequence is known to map to sequences that are non-contiguous.

In some cases, phasing is performed at greater than 90% accuracy. In some cases, the read-set is generated by binning the labeled nucleic acid segments that comprise a same label. In some cases, at least 1% of the labeled nucleic acid segments in the read-set spans a distance of at least 50 kB on the first nucleic acid molecule.

Also disclosed herein are methods of labeling a plurality of nucleic acid molecules. In some cases, methods comprise binding, such as by cross-linking, a plurality of nucleic acid molecules to a plurality of nucleic acid binding moieties to form a plurality of nucleic acid complexes; cleaving, such as by digesting, the nucleic acid complexes such that phosphodiester backbones are cleaved to expose nucleic acid ends; tagging the plurality of nucleic acid complexes such that a first complex is tagged by a first nucleic acid tag having a first sequence and a second complex is tagged by a first nucleic acid tag having a second sequence; and tagging the plurality of nucleic acid complexes such that a first complex is tagged using a second nucleic acid tag. Some methods comprise tagging the first complex using a third nucleic acid tag. Some methods comprise tagging the first complex using a fourth nucleic acid tag. Some methods comprise sequencing a nucleic acid of the first complex such that the second tag, the first tag and nucleic acid molecule sequence adjacent to the first tag are obtained in a single read. Some methods comprise sequencing a plurality of nucleic acid complexes to obtain a plurality of reads comprising a read comprising a second tag sequence, a first tag sequence and first nucleic acid molecule sequence adjacent to the first tag sequence, and a read comprising a second tag sequence, a first tag sequence and second nucleic acid molecule sequence adjacent to the first tag sequence. In some cases, the method comprises assigning a first nucleic acid molecule sequence and a second nucleic acid molecule sequence to a common phase if the first nucleic acid molecule sequence read and the second nucleic acid molecule sequence read share a common second tag sequence and a common first tag sequence. Some methods comprise assigning a first nucleic acid molecule sequence and a second nucleic acid molecule sequence to a common scaffold if the first nucleic acid molecule sequence read and the second nucleic acid molecule sequence read share both a common second tag sequence and a common first tag sequence. In some cases, the method comprises assigning a first nucleic acid molecule sequence and a second nucleic acid molecule sequence to a separate phase if the first nucleic acid molecule sequence read and the second nucleic acid molecule sequence read do not share a common second tag sequence and a common first tag sequence. In some cases, the method comprises assigning a first nucleic acid molecule sequence and a second nucleic acid molecule sequence to distinct scaffolds if the first nucleic acid molecule sequence read and the second nucleic acid molecule sequence read share a common second tag sequence and a common first tag sequence, but the non-tag sequence is known to map to contigs that are not in phase, for example because they map to different chromosomes. That is, in some cases distinct molecules will be commonly or identically tagged, particularly when a small number of tags and small number of iterations are used. In some cases, the cleaving comprises chemical, enzymatic, and/or mechanical protocols such as sonicating, shearing, non-specific endonuclease digestion, specific endonuclease digestion, and enzymatic cleavage, such as with a topoisomerase, a base-repair enzyme, or a transposases such as Tn5. In some cases, the tagging comprises hybridized a tag to a nucleic acid end. Alternatively, tags are ligated or otherwise covalently attached to exposed nucleic acid ends. In some cases, nucleic acid molecules sharing common tag sequences map to a common scaffold. In some cases, nucleic acid molecules sharing common tag sequences map to a common phase. In some cases, at least 80% of nucleic acid sequences are assigned to a contig comprising at least one other nucleic acid sequence. In some cases, at least 80% of nucleic acid sequences are assigned to a phase comprising at least one other nucleic acid sequence. In some cases, at least 80% of the cleaved phosphodiester backbones are tagged. In some cases, a first nucleic acid sequence and a second nucleic acid sequence separated by greater than 10 kb in a genome are assigned to a common scaffold. In some cases, a first nucleic acid sequence and a second nucleic acid sequence separated by greater than 10 kb in a genome are assigned to a common phase. In some cases, a first nucleic acid sequence and a second nucleic acid sequence separated by greater than 50 kb in a genome are assigned to a common scaffold. In some cases, a first nucleic acid sequence and a second nucleic acid sequence separated by greater than 50 kb in a genome are assigned to a common phase.

Also disclosed herein are methods of packaging a nucleic acid sample into phase-tagged fragments. Some methods of packaging a nucleic acid sample into phase-tagged fragments comprise the steps of (a) forming intramolecular phosphodiester backbone-independent bonds, such as covalent bonds or non-covalent linkages connecting separate regions of the nucleic acid such as via an intermediary molecule, to bind a constituent of the nucleic acid sample, (b) cleaving the constituent of the nucleic acid sample to expose at least one pair of internal double-strand break ends, (c) tagging the at least one pair of internal double-strand break ends with a first tag set, (d) tagging the at least one pair of internal double-strand break ends with a second tag set, and (e) tagging the at least one pair of internal double-strand break ends with a third tag set, wherein the first tag set, the second tag set and the third tag set independently convey phase information. In some cases, tagging comprises ligating an oligonucleotide tag to the at least one pair of internal double-strand break ends. In some cases, the method comprises tagging the at least one pair of internal double-strand break ends with a fourth tag set. In some cases, the constituent of the nucleic acid sample is cross-linked to an association molecule. In some cases, the association molecule comprises amino acids, such as amino acids linked into polypeptide beads. In some cases, forming intramolecular phosphodiester backbone-independent bonds comprises cross-linking. In some cases, forming intramolecular phosphodiester backbone-independent bonds comprises cross-linking with a fixative agent. In some cases, the fixative agent is formaldehyde, psoralen, or UV light. In some cases, the first tag set and the second tag set are non-identical. In some cases, the third tag set is non-identical to the first tag set and the second tag set. In some cases, the first tag set is less than 10 bases (e.g. less than 9, 8, 7, 6, 5, 4, 3, or 2 bases) in length. In some cases, the second tag set is less than 10 bases (e.g. less than 9, 8, 7, 6, 5, 4, 3, or 2 bases) in length. In some cases, the third tag set is less than 10 bases (e.g. less than 9, 8, 7, 6, 5, 4, 3, or 2 bases) in length. Non-identical tag set patterns between two sequence reads indicate that sequence reads are likely derived from different constituents of the nucleic acid sample. Common tag set patterns between two sequence reads may indicate that the sequence reads are derived from the same constituent of the nucleic acid sample or possibly form two different constituents. This may occur when two constituents co-segregate throughout each iteration of the tagging process and receive common first, second, third and/or fourth tag sets. For samples comprising large numbers of constituents, this number may be non-zero.

Also disclosed herein are nucleic acid compositions. In some cases nucleic acid compositions from an organism comprises a nucleic acid library, wherein each library constituent comprises a nucleic acid comprising a nucleic acid sample segment, a first tag, a second tag, and a third tag. In some cases, a difference between a first library constituent and a second library constituent in any one of a first tag sequence, second tag sequence and third tag sequence independently indicates that the first library constituent and the second library constituent do not comprise nucleic acid segments sharing a common phase in the organism. In some cases, the first tag is less than 10 bases (e.g. 9, 8, 7, 6, 5, 4, 3, or 2 bases) in length. In some cases, the second tag is less than 10 bases (e.g. 9, 8, 7, 6, 5, 4, 3, or 2 bases) in length. In some cases, the third tag is less than 10 bases (e.g. 9, 8, 7, 6, 5, 4, 3, or 2 bases) in length. In some cases, the first tag and the second tag are non-identical. In some cases, the third tag is non-identical to the first tag and the second tag. In some cases, each library constituent has been formed by ligating a nucleic acid sample segment, a first tag, a second tag, and a third tag.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein) of which:

FIG. 1A is a diagram illustrating the scheme of distributing, ligating, and pooling cross-linked chromatin aggregates for barcode and/or adapter attachment.

FIG. 1B is an illustration of a barcoded cross-linked chromatin aggregate.

FIG. 2A is a diagram illustrating the minimum number of barcodes required as a function of the probability of a noise read in read cluster for various values of noise rate (f).

FIG. 2B is a diagram illustrating the maximum amount of DNA sampled (ng) as a function of reads per chromatin aggregate for various values of noise rate (f).

DETAILED DESCRIPTION OF THE INVENTION

Figure 3:
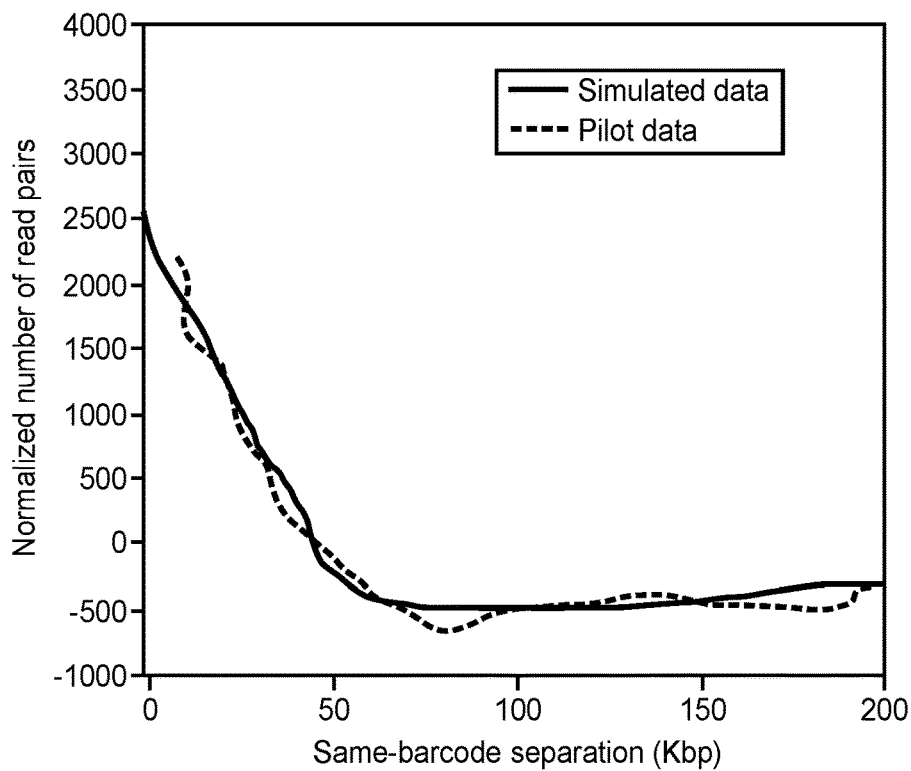
FIG. 3 is a diagram illustrating simulated and experimental results of normalized numbers of read pairs as a function same-barcode separation (kbp).

The present disclosure provides methods of sample preparation for next generation sequencing (NGS) platforms in which phase or linkage information can be deduced from tagged short reads. Provided herein are methods and compositions for iteratively labeling bound DNA clusters with barcodes, such that barcode combinations comprising at least two barcodes can be used to infer phase information. Binding single DNA molecules, for example to association molecules comprising proteins, such as histones, transcription factors, and transposases; non-protein organic molecules; and nanoparticles, allows fragments arising from a single molecule of DNA to remain associated by proximity even while not physically linked. Barcodes and/or adapters are attached, for example through ligation or hybridization, in an iterative manner to free nucleic acid ends. Phase information is determined from sequence reads by comparing the unique barcode combinations. These methods are used for the preparation of sequencing libraries for NGS platforms and allow the resulting sequence reads to be phased with high accuracy.

Through the methods herein, nucleic acids in a sample are internally tagged so that, upon sequencing the tags and adjacent sample sequence, information regarding phase or physical linkage of the adjacent sample sequence is provided. As a result, sequences far removed from one another on a nucleic acid molecule are confidently inferred to have originated from a common molecule.

A library is prepared by forming nucleic acid complexes. Nucleic acid complexes are formed by contacting nucleic acids to a population of binding agents. The binding agents are administered at a concentration such that a given binding agent is likely to bind one and only one nucleic acid. In exemplary embodiments, the binding agents are chromatin components added to naked DNA, although other binding agents are contemplated such as nucleic acid binding proteins including transcription factors and transposases; non-protein organic molecules such as protamine, spermine, spermidine or other positively charged molecules; and nanoparticles such as nanoparticles comprising silicon, platinum, and/or magnetic materials. In some cases, binding agents are treated with a cross-linking reagent such as formaldehyde, psoralen, or UV light.

Binding agents bind to individual nucleic acids at multiple points of contact in some cases, such that the segments at these points of contact are held together independent of their common phosphodiester backbone.

Complexes are then treated so as to induce at least one double-stranded break. In exemplary embodiments, treatment to induce at least one double-stranded break comprises digesting by contacting with a restriction endonuclease, although other treatments are contemplated. Other treatments can include but are not limited to sonication, shearing, specific endonuclease treatment, non-specific endonuclease treatment, and enzymatic cleavage such as with a topoisomerase, a base-repair enzyme, or a transposase such as Tn5.

Complexes are then divided into distinct volumes, wherein some different volumes have different tags. Tags may be 2, 3, 4, 5, 6, 7, 8, 9, 10 bases or longer. In some cases, each volume has a tag comprising a unique sequence. In some cases, one volume has tags comprising two or more unique sequences. In some cases, two or more volumes have tags comprising a shared unique sequence. Tags are attached to the free ends of complexes in each volume. Tags can be attached by various methods, including but not limited to hybridization, ligation, and double-stranded break repair, such that in many cases, the complexes in a volume are commonly tagged.

The probability of receiving a unique tag is a function of the number of volumes into which the complexes are divided. For example, complexes are divided randomly among 64 volumes, each with a unique tag of at least 3 bases, and the tags are attached to complexes with 100% efficiency, that is every complex receives a tag. Following tag attachment, the complexes from the 64 volumes are pooled together. When sub-sampling two complexes from the pool, the probability that the two complexes have a common tag is 1/64. Alternately, if 8 volumes are used, then the probability 1/8.

In some cases, a very large number of volumes, each with a long, unique tag of for example, 10 or more bases, may be sufficient to tag the complexes with enough distinction for downstream operations, such that a single iteration of tagging is sufficient to distinguish among complexes.

As an alternative, singly tagged complexes are bulked, in many cases randomly, into at least one common volume and then re-divided into different volumes for a second round of tagging, again assuming 100% efficiency in tagging. As a result of this iteration, the probability of two complexes sub-sampled from the pooled complexes sharing a common tag pattern decreases exponentially, to the [1/((number of volumes)2)]. Thus, for 8 volumes, the chance of common tagging is 1/64 after a second iteration of bulking and tagging.

By repeating this iterative process, one reduces the chance of common tag patterns to whatever level needed for downstream sequence analysis. For example, at 3 iterations the probability of common tagging for an 8 volume set-up is 1/512, at 4 iterations 1/4096 (using only 32 volumes and 8 bases of information tagging), and so on.

This process is both iterative and flexible. By using smaller numbers of volumes and larger numbers of iterations, one can achieve a common result. For example, using a 96 well plate and two iterations, one achieves over 9,000 tag variants. Similarly using 5 iterations of an 8 volume division and tagging, one achieves over 32,000 tag variants in a total of less than half of a single 96-well plate, and using substantially smaller and less expensive tags.

Upon reaching the desired level of tagging, complexes are disassembled, freeing the multiply tagged nucleic acid fragments. Nucleic acids are no longer physically attached to one another, but their tag patterns indicate their complex of origin. Fragments having nonmatching tag patterns are identified as not originating from a common molecule in the sample. Fragments having common tag patterns are either from a common complex or represent two complexes that, by chance, co-segregated throughout each iteration of the process. For samples comprising large numbers of nucleic acids, this number may be non-zero—that is, not all commonly tagged fragments will map to a single molecule. In many cases, however, the sequence adjacent to the tags (that is, the sample sequence of each fragment) is used to inform assembly. For example, sequences that share common tags and that assemble into a common contig are confidently concluded to be in phase. Alternately if contig information is independently available, it can be used to aide in phase determination.

Thus using this approach, internal tags are added to nucleic acids of a sample, such that reads of the molecule are grouped by their tags into a common phase or physical molecule/origin.

Next-generation sequencing (NGS) technologies have significantly impacted the field of genomics, allowing genomic DNA to be sequenced at unprecedented speeds. Developments in sequencing technologies, such as, for example, massive parallelization of chemical sequencing reactions, micro- to nano-scale reaction volumes, and improved computational analysis methods, have placed a wide range of genomic analyses within the capabilities of many laboratories. These new techniques and methodologies can reduce the cost of operation and simplify sample preparation protocols, and genomic analyses can be more widely accessible. Current NGS platforms produce sequencing reads between approximately 100 bases and 700 bases in length. Some sequencing systems can produce even longer read lengths, such as up to 15,000 bases. However, longer read lengths are generally associated with higher error rates. As genomic DNA contains large amounts of sequence information, lower error rates can be advantageous in that genomic segments may not need to be redundantly sequenced to determine, for example, if a mutation in a chromosome is a verifiable mutation or a result of operational error. Shorter reads, in addition to being relatively less expensive, are generally associated with lower error rates, and may be preferred. However, data produced from short read lengths present a challenge to de novo assembly, for example, with diploid genomes which generally contain two copies of each chromosome, generally referred to as homologous chromosomes. The alleles on homologous chromosomes may be different and result in different phenotypes of the same genes. A combination of alleles or a set of single nucleotide polymorphisms (SNPs) found on the same chromosome can be generally referred to as a haplotype. The lack of linkage information between sequencing reads and the presence of large repetitive repeats in the genome can make it challenging to confidently associate variants with haplotypes, also referred to as phasing, over long-distances, for example, if the allelic variants are separated by a greater distance than the longest single read. However, phasing variations are increasingly important, for example, to characterize genetic variants and disease susceptibility, infer human demographic history, and infer points of recombination.

With current technologies, large volumes of high-throughput sequencing data can be obtained relatively inexpensively. Industry standard sequencing technologies can produce billions of sequence reads of up to 250 nucleotides (nt) in length, allowing high coverage human genome resequencing, or resequencing of any organism having a completed or draft genome available. The reads themselves can come from DNA fragments that are typically 300 to 600 base pairs (bp) in length. This configuration can allow fast and accurate determination of single nucleotide variant positions or single nucleotide polymorphisms (SNPs) in a given genome (Abecasis, et al., 2010; Nielsen, et al., 2011).

It may be challenging to use these data for generating a complete picture of the genome of an individual. For example, the assignment of genomic variants to either of two copies of each chromosome, which can be referred to as haplotype phasing, can be challenging using short-read data (He, et al., 2010). Structural variants can also be difficult to detect or pinpoint at single base pair resolution. Inferring phase can be done computationally with population data by learning which variants tend to be linked. However, challenges remain for phasing rare sequence variants (Pistis, et al., 2014). Accurate analysis of sequence variants and variations can be useful for the characterization of large structural variants and compound heterozygotes (Browning & Browning, 2011; Tewhey, et al., 2011) and requires new approaches for haplotype phasing.

Several approaches for experimental phasing are available. Longer sequencing reads from longer DNA fragments can be used to observe haplotype phase. These technologies are in early stages of development and may not be economically competitive with short read technologies (Munroe & Harris, 2010). Mate-pair data can also be used for haplotype phasing (Kim, et al., 2007), but may require lengthy protocols. Mate-pair libraries can be limited to input DNA between 5-10 kilobase pairs (kbp) in length and may require SNPs to be present at both sequenced ends to provide phasing information.

Other technologies for efficient haplotype phasing comprise generating read-sets that are derived from an individual DNA molecule and are thus haplotype phased. The known linkage of reads within a read-set can allow short reads to be used for haplotype phasing and many not require long, contiguous reads. Read-sets that derive from an individual DNA molecule and are haplotype phased can be constructed via various protocols, such as through the use of barcoded sequencing libraries constructed via microfluidic emulsions, dilution and subdivision (Kaper, et al., 2013), or virtual compartmentalization using a property of the Tn5 transposase (Adey, et al., 2014). Barcoded sequencing libraries via microfluidic emulsions may utilize highly specialized methods, select sizes of DNA molecules, and specialized instruments. Dilution and subdivision methods may require select sizes of DNA molecules, potentially a maximum of 10 kbp DNA, and PCR amplification steps, which can introduce amplification bias (McCoy, et al., 2014).

The present disclosure provides methods and compositions for generating low-cost read-sets based on barcoding cross-linked nucleic acid molecules. The methods and compositions herein allow for fewer limits on the size of the input DNA and do not require specialized instruments. In some cases, the nucleic acid molecules are cross-linked to in vitro assembled chromatin, or chromatin that is reconstituted in vitro. Chromatin can be reconstituted from molecules of DNA and can serve as a platform for tagging individual DNA molecules with unique barcodes and/or sets of barcodes for downstream, long-range genomic variant phasing.

Methods and compositions of the present disclosure produce data that improve the length, accuracy, and completeness of phased haplotypes using sequencing data from short-reads. Long-range data of the type produced through the methods herein improve de novo genome assembly as much as 100-fold (Putnam, et al., 2015).

Disclosed herein are methods that can be used to label and/or associate polynucleotides or sequence segments thereof and methods to utilize that data for various applications. The methods and compositions of the present disclosure improve genome assembly by producing highly accurate, long-range phasing. The disclosure provides methods that produce a highly contiguous and accurate human genomic assembly with less than 10,000, 20,000, 50,000, 100,000, 200,000, 500,000, 1 million, 2 million, 5 million, 10 million, 20 million, 30 million, 40 million, 50 million, 60 million, 70 million, 80 million, about 90 million, about 100 million, about 200 million, about 300 million, about 400 million, about 500 million, about 600 million, about 700 million, about 800 million, about 900 million, or about 1 billion read pairs. The methods provided herein phase, or assign physical linkage information to, about 50%, 60%, 70%, 75%, 80%, 85%, 90%, 91%, 92%, 93%, 94%, 95%, 96%, 97%, 98%, 99% or more of heterozygous variants in a human genome with about 50%, 60%, 70%, 75%, 80%, 85%, 90%, 91%, 92%, 93%, 94%, 95%, 96%, 97%, 98%, 99%, or greater accuracy.

As used herein and in the appended claims, the singular forms "a," "and," and "the" include plural referents unless the context clearly dictates otherwise. Thus, for example, reference to "contig" includes a plurality of such contigs and reference to "phasing a plurality of contigs" includes one or more methods for phasing and equivalents thereof known to those skilled in the art, and so forth.

The use of "and" means "and/or" unless stated otherwise. Similarly, "comprise," "comprises," "comprising," "include," "includes," and "including" are interchangeable and not intended to be limiting, and refer to the nonexclusive presence of the recited element, leaving open the possibility that additional elements are present.

The term "read," "sequence read," or "sequencing read" as used herein, refers to a fragment of DNA sequence information in which the sequence has been determined.

The term "contig" and "contigs" as used herein, refers to contiguous regions of DNA sequence. "Contigs" can be determined by any number methods known in the art, such as, by comparing sequencing reads for overlapping sequences, and/or by comparing sequencing reads against a databases of known sequences in order to identify which sequencing reads have a high probability of being contiguous. For many genomes and other large-scale sequencing projects, contigs are available and can be readily obtained, but physical linkage information regarding whether two or more contigs represent sequence from a single physical nucleic acid molecule, and how the contigs are to be positioned relative to one another, can be difficult to obtain. This difficulty is largely due to the presence of repetitive regions comprising sequence information that does not uniquely map to any single contig.

The term "subject" as used herein can refer to any eukaryotic or prokaryotic (eubacterial or archaeal) organism. For example, a subject can be a mammal, such as a human.

The terms "polynucleotide," "nucleotide," "nucleic acid" and "oligonucleotide" are used interchangeably. They generally refer to a polymeric form of nucleotides of any length, either deoxyribonucleotides or ribonucleotides, or analogs thereof. Polynucleotides comprise base monomers that are joined at their ribose backbones by phosphodiester bonds. Polynucleotides may have any three dimensional structure, and may perform any function, known or unknown. The following are non-limiting examples of polynucleotides: coding or non-coding regions of a gene or gene fragment, intergenic DNA, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), small nucleolar RNA, ribozymes, complementary DNA (cDNA), which is a DNA representation of mRNA, usually obtained by reverse transcription of messenger RNA (mRNA) or by amplification; DNA molecules produced synthetically or by amplification, genomic DNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. Generally, an oligonucleotide comprises only a few bases, while a polynucleotide can comprise any number but is generally longer, while a nucleic acid can refer to a polymer of any length, up to and including the length of a chromosome or an entire genome. Also, the term nucleic acid is often used collectively, such that a nucleic acid sample does not necessarily refer to a single nucleic acid molecule; rather it may refer to a sample comprising a plurality of nucleic acid molecules. The term nucleic acid can encompass double- or triple-stranded nucleic acids, as well as single-stranded molecules. In double- or triple-stranded nucleic acids, the nucleic acid strands need not be coextensive, e.g., a double-stranded nucleic acid need not be double-stranded along the entire length of both strands. The term nucleic acid can encompass any chemical modification thereof, such as by methylation and/or by capping. Nucleic acid modifications can include addition of chemical groups that incorporate additional charge, polarizability, hydrogen bonding, electrostatic interaction, and functionality to the individual nucleic acid bases or to the nucleic acid as a whole. Such modifications may include base modifications such as 2'-position sugar modifications, 5-position pyrimidine modifications, 8-position purine modifications, modifications at cytosine exocyclic amines, substitutions of 5-bromo-uracil, backbone modifications, unusual base pairing combinations such as the isobases isocytidine and isoguanidine, and the like.

The term "target polynucleotide" generally refers to nucleic acid molecules or polynucleotides to be analyzed, modified, or characterized. "Target polynucleotide" may be used to refer to a double-stranded nucleic acid molecule comprising a target sequence on one or both strands, or a single-stranded nucleic acid molecule comprising a target sequence, and may be derived from any source of or process for isolating or generating nucleic acid molecules. A target polynucleotide may comprise at least one (e.g. 1, 2, 3, 4, 5, 6, 7, 8, 9, 10, or more) target sequences, which may be the same or different. In general, different target polynucleotides comprise different sequences, such as one or more different nucleotides or one or more different target sequences.

The term "naked DNA" as used herein can refer to DNA that is substantially free of complexed DNA binding proteins. For example, it can refer to DNA complexed with less than about 10%, about 5%, or about 1% of the endogenous proteins found in the cell nucleus, or less than about 10%, about 5%, or about 1% of the endogenous DNA-binding proteins regularly bound to the nucleic acid in vivo, or less than about 10%, about 5%, or about 1% of an exogenously added nucleic acid binding protein or other nucleic acid binding moiety, such as a nanoparticle. In some cases, naked DNA refers to DNA that is not complexed to DNA binding proteins.

The term "hybridized" as applied to a polynucleotide refers to a polynucleotide in a complex that is stabilized via hydrogen bonding between bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. The hybridization reaction may constitute a step in a more extensive process, such as the initiation of a PCR reaction, or the enzymatic cleavage of a polynucleotide by a ribozyme. A sequence hybridized with a given nucleic acid is referred to as the "complement" or "reverse-complement" of the given molecule if its sequence of bases over a given region is capable of complementarily binding those of its binding partner, such that, for example, A-T, A-U, and G-C and G-U base pairs are formed.

The terms "polypeptide" and "protein" are often used interchangeably and generally refer to a polymeric form of amino acids, or analogs thereof bound by polypeptide bonds. Polypeptides and proteins can be polymers of any length. Polypeptides and proteins can have any three dimensional structure, and may perform any function, known or unknown. Polypeptides and proteins can comprise modifications, including phosphorylation, lipidation, prenylation, sulfation, hydroxylation, acetylation, formation of disulfide bonds, and the like. In some cases "protein" refers to a polypeptide having a known function or known to occur naturally in a biological system, but this distinction is not always adhered to in the art.

The terms "phase" and "phase determination" as used herein, generally refer to haplotype phasing, the assignment of genomic variants to either of two copies of a chromosome, and the assignment of a physical linkage relationship to two or more nucleic acid fragments, segments, and/or molecules on a contig or scaffold. A haplotype can refer to a combination of alleles or to a set of single nucleotide polymorphisms (SNPs) found on the same chromosome. Phasing can refer to the assignment of a first sequence read to a physical linkage relationship with a second sequence read. In some cases phase determination is guided by the determination of a common molecule of origin for a pair of sequence reads. In some cases phase determination is guided by at least one of 1) determination of the chance of two sets of tags occurring by chance on a pair of sequence reads, 2) determining the contig or contigs or scaffold or scaffolds onto which a set of sequence reads maps, 3) determining common polymorphisms among a set of sequence reads that indicate that the sequences arose from a common molecule or distinct molecules having identical sequences (e.g., multiple copies of a common nucleic acid molecule), and 4) determining the frequency or strength of a signal indicating that two or more sequence reads arise from a common source molecule or separate copies of a common source molecule. One of skill in the art is familiar with additional factors involved in phase determination.

Similarly, the term 'assembling' as used herein refers to assigning sequence reads to one or more contigs or scaffolds. The contigs or scaffolds or contigs and scaffolds are previously existent in some cases, while in other cases the sequence reads are assigned to scaffolds, contigs or scaffolds and contigs that are generated or revised concurrently with sequence assembly. In some cases assembling sequence reads comprises determining molecule of origin information for a set of sequence reads. In some cases assembling sequence reads comprises determining phase information for as set of sequence reads. One of skill in the art is familiar with additional factors involved in assembling sequence reads.

The term "scaffold" as used herein generally refers to contigs separated by gaps of known length but unknown sequence or separated by unknown length but known to reside on a single molecule, or ordered and oriented sets of contigs that are linked to one another by mate pairs of sequencing reads. In cases where contigs are separated by gaps of known length, the sequence of the gaps may be determined by various methods, including PCR amplification followed by sequencing (for smaller gaps) and bacterial artificial chromosome (BAC) cloning methods followed by sequencing (for larger gaps).

The term "about" as used herein to describe a number, unless otherwise specified, refers to a range of values including that number plus or minus 10%.

As used herein, the term 'segregate' means to occur independently throughout at least one iteration of a labeling process. Thus, two barcodes segregate independently if the chance of addition of one barcode is independent of the chance of addition of the second barcode. As an alternative, if two barcodes are attached to one another prior to any ligation process, they would be found to 'co-segregate' throughout a labeling process in that the occurrence of one bar code is dependent upon the occurrence of the second barcode. Such usage resembles the usage of the terms in genetics in the context of trait inheritance.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

Nucleic Acid Complexes

Nucleic acids for can be bound to form nucleic acid complexes. In some cases, nucleic acid complexes comprise nucleic acids bound to a plurality of association molecules or moieties, such as polypeptides; non-protein organic molecules; and nanoparticles. Binding agents bind to individual nucleic acids at multiple points of contact in some cases, such that the segments at these points of contact are held together independent of their common phosphodiester backbone.

In some cases, binding a nucleic acid comprises forming linkages, for example covalent linkages, between segments of a nucleic acid molecule. Linkages can be formed between distant segments of a nucleic acid molecule. In some cases, binding a nucleic acid to form a nucleic acid complex comprises cross-linking a nucleic acid to an association molecule or moiety (herein also referred to as a nucleic acid binding molecule or moiety). In some cases, association molecules comprise amino acids, including but not limited to peptides and proteins such as DNA binding proteins. Exemplary DNA binding proteins include native chromatin constituents such as histone, for example Histones 2A, 2B, 3A, 3B, 4A, and 4B. In some cases, the plurality of nucleic acid binding moieties comprises reconstituted chromatin or in vitro assembled chromatin. Chromatin can be reconstituted from DNA molecules that are about 150 kbp in length. In some cases, chromatin is reconstituted from DNA molecules that are at least 50, 100, 125, 150, 200, 250 kbp or more in length. In some cases, binding proteins comprise transcription factors or transposases. Non-protein organic molecules are also compatible with the disclosure herein, such as protamine, spermine, spermidine or other positively charged molecules. In some cases, the association molecules comprise nanoparticles, such as nanoparticles having a positively charged surface. A number of nanoparticle compositions are compatible with the disclosure herein. In some embodiments the nanoparticles comprise silicon, such as silicon coated with a positive coating so as to bind negatively charged nucleic acids. In some cases, the nanoparticle is a platinum-based nanoparticle. The nanoparticles magnetic nanoparticles, which facilitate the isolation of the cross-linked sequence segments in some cases. In some cases, the nanoparticle is an amine-coated nanoparticle, a gold-containing nanoparticle, a silver-containing nanoparticle, a DNA intercalator or any derivatives thereof, a copper-containing nanoparticle, and combinations thereof.

A nucleic acid is bound to an association molecule by various methods consistent with the disclosure herein. In some cases, a nucleic acid is cross-linked to an association molecule. Methods of crosslinking include ultraviolet irradiation, chemical and physical (e.g., optical) crosslinking. Non-limiting examples of chemical crosslinking agents include formaldehyde and psoralen (Solomon et al., Proc. Natl. Acad. Sci. USA 82:6470-6474, 1985; Solomon et al., Cell 53:937-947, 1988). In some cases, cross-linking is performed by adding a solution comprising about 2% formaldehyde to a mixture comprising the nucleic acid molecule and chromatin proteins. Other non-limiting examples of agents that can be used for cross-linking DNA include, but are not limited to, mitomycin C, nitrogen mustard, melphalan, 1,3-butadiene diepoxide, cis diaminedichloroplatinum(II) and cyclophosphamide. In some cases, the cross-linking agent forms cross-links that bridge relatively short distances—such as about 2 Å, 3 Å, 4 Å, or 5 Å. In some cases, binding and/or cross-linking is performed while the plurality of nucleic acids is within or inside of a cell. In some cases, binding and/or cross-linking is performed while the plurality of nucleic acids is external to or outside a cell.

Crosslinking occurs between or among association molecules, between association molecules and nucleic acids, or both between or among association molecules and between association molecules and nucleic acids in various embodiments. In some cases, nucleic acid complexes, for example nucleic acids bound to in vitro assembled chromatin (herein referred to as chromatin aggregates) are attached to a solid support, including but not limited to beads, for example magnetic beads.

Chromatin Reconstitution

Reconstituted chromatin as a binding moiety is accomplished by a number of approaches. Reconstituted chromatin as contemplated herein is used broadly to encompass binding of a broad number of binding moieties to a naked nucleic acid. Binding moieties include histones and nucleosomes, but in some interpretations of reconstituted chromatin also other nuclear proteins such as transcription factors, transposons, or other DNA or other nucleic acid binding proteins, spermine or spermidine or other non-polypeptide nucleic acid binding moieties, nanoparticles such as organic or inorganic nanoparticle nucleic acid binding agents.

In some cases, reconstituted chromatin is used in reference to the reassembly of native chromatin constituents or homologues of native chromatin constituents onto a naked nucleic acid, such as reassembly of histones or nucleosomes onto a native nucleic acid.

Two approaches to reconstitute chromatin include (1) ATP-independent random deposition of histones onto DNA, and (2) ATP-dependent assembly of periodic nucleosomes. This disclosure contemplates the use of either approach with one or more methods disclosed herein. Examples of both approaches to generate chromatin can be found in Lusser et al. ("Strategies for the reconstitution of chromatin," Nature Methods (2004), 1(1):19-26), which is incorporated herein by reference in its entirety.

Other approaches to reconstituting chromatin, either strictly defined as nucleosome or histone addition to naked nucleic acids, or more broadly defined as the addition of any moiety to a naked nucleic acid, are contemplated herein and known to one of skill in the art, and neither the composition of chromatin nor the approach to its reconstitution should be considered limiting in some embodiments.

Cleaving Nucleic Acid Molecules

Nucleic acid molecules, such as bound nucleic acid molecules in nucleic acid complexes, can be cleaved to expose internal nucleic acid ends and create double-stranded breaks. In some cases, a nucleic acid molecule, such as a nucleic acid molecule in a nucleic acid complex, is cleaved to expose nucleic acid ends and form at least two fragments or segments that are not physically linked at their phosphodiester backbone. Various methods can be used to cleave internal nucleic acid ends and/or generate fragments derived from a nucleic acid, including but not limited to mechanical, chemical, and enzymatic methods such as shearing, sonication, nonspecific endonuclease treatment, or specific endonuclease treatment. Alternate approaches involve enzymatic cleavage, such as with a topoisomerase, a base-repair enzyme, a transpose such as Tn5, or a phosphodiester backbone nicking enzyme.

In some cases, a nucleic acid is cleaved by digesting. Digestion can comprise contacting with a restriction endonuclease. Restriction endonucleases can be selected in light of known genomic sequence information to tailor an average number of free nucleic acid ends that result from digesting. Restriction endonucleases can cleave at or near specific recognition nucleotide sequences known as restriction sites. Restriction endonucleases having restriction sites with higher relative abundance throughout the genome can be used during digestion to produce a greater number of exposed nucleic acid ends compared to restriction endonucleases having restriction sites with lower relative abundance, as more restrictions sites can result in more cleaved sites. In some cases, restriction endonucleases with non-specific restriction sites, or more than one restriction site, are used. A non-limiting example of a non-specific restriction site is CCTNN. The bases A, C, G, and T refer to the four nucleotide bases of a DNA strand—adenine, cytosine, guanine, and thymine. The base N represents any of the four DNA bases—A, C, G, and T. Rather than recognizing a specific sequence for cleavage, an enzyme with the corresponding restriction site can recognize more than one sequence for cleavage. For example, the first five bases that are recognized can be CCTAA, CCTAT, CCTAG, CCTAC, CCTTA, CCTTT, CCTTG, CCTTC, CCTCA, CCTCT, CCTCG, CCTCC, CCTGA, CCTGT, CCTGG, or CCTGC (16 possibilities). In some cases, use of an enzyme with a non-specific restriction site results in a larger number of cleavage sites compared to an enzyme with a specific restriction site. Restriction endonucleases can have restriction recognition sequences of at least 4, 5, 6, 7, 8 base pairs or longer. Restriction enzymes for digesting nucleic acid complexes can cleave single-stranded and/or double-stranded nucleic acids. Restriction endonucleases can produce single-stranded breaks or double-stranded breaks. Restriction endonuclease cleavage can produce blunt ends, 3' overhangs, or 5' overhangs. A 3' overhang can be at least 1, 2, 3, 4, 5, 6, 7, 8, or 9 bases in length or longer. A 5' overhang can be at least 1, 2, 3, 4, 5, 6, 7, 8, or 9 bases in length or longer. Examples of restriction enzymes include, but are not limited to, AatII, Acc65I, AccI, AciI, AclI, AcuI, AfeI, AflII, AflIII, AgeI, AhdI, AleI, AluI, AlwI, AlwNI, ApaI, ApaLI, ApeKI, ApoI, AscI, AseI, AsiSI, AvaI, AvaII, AvrII, BaeGI, BaeI, BamHI, BanI, BanII, BbsI, BbvCI, BbvI, BccI, BceAI, BcgI, BciVI, BclI, BfaI, BfuAI, BfuCI, BglI, BglII, BlpI, BmgBI, BmrI, BmtI, BpmI, Bpu10I, BpuEI, BsaAI, BsaBI, BsaHI, BsaI, BsaJI, BsaWI, BsaXI, BscRI, BscYI, BsgI, BsiEI, BsiHKAI, BsiWI, BslI, BsmAI, BsmBI, BsmFI, BsmI, BsoBI, Bsp1286I, BspCNI, BspDI, BspEI, BspHI, BspMI, BspQI, BsrBI, BsrDI, BsrFI, BsrGI, BsrI, BssHII, BssKI, BssSI, BstAPI, BstBI, BstEII, BstNI, BstUI, BstXI, BstYI, BstZ17I, Bsu36I, BtgI, BtgZI, BtsCI, BtsI, Cac8I, ClaI, CspCI, CviAII, CviKI-1, CviQI, DdeI, DpnI, DpnII, DraI, DraIII, DrdI, EacI, EagI, EarI, EciI, Eco53kI, EcoNI, EcoO109I, EcoP15I, EcoRI, EcoRV, FatI, FauI, Fnu4HI, FokI, FseI, FspI, HaeII, HaeIII, HgaI, HhaI, HincII, HindIII, HinfI, HinP1I, HpaI, HpaII, HphI, Hpy166II, Hpy188I, Hpy188III, Hpy99I, HpyAV, HpyCH4III, HpyCH4IV, HpyCH4V, KasI, KpnI, MboI, MboII, MfeI, MluI, MlyI, MmeI, MnlI, MscI, MseI, MslI, MspA1I, MspI, MwoI, NaeI, NarI, Nb.BbvCI, Nb.BsmI, Nb.BsrDI, Nb.BtsI, NciI, NcoI, NdeI, NgoMIV, NheI, NlaIII, NlaIV, NmeAIII, NotI, NruI, NsiI, NspI, Nt.AlwI, Nt.BbvCI, Nt.BsmAI, Nt.BspQI, Nt.BstNBI, Nt.CviPII, PacI, PaeR7I, PciI, PflFI, PflMI, PhoI, PleI, PmeI, PmlI, PpuMI, PshAI, PsiI, PspGI, PspOMI, PspXI, PstI, PvuI, PvuII, RsaI, RsrII, SacI, SacII, SalI, SapI, Sau3AI, Sau96I, SbfI, ScaI, ScrFI, SexAI, SfaNI, SfcI, SfiI, SfoI, SgrAI, SmaI, SmlI, SnaBI, SpeI, SphI, SspI, StuI, StyD4I, StyI, SwaI, T, Taqαl, TfiI, TliI, TseI, Tsp45I, Tsp509I, TspMI, TspRI, Tth111I, XbaI, XcmI, XhoI, XmaI, XmnI, and ZraI.

Attaching Oligonucleotides to Nucleic Acid Molecules

Oligonucleotides comprising labels, tags, adaptors, sequencing adapters (herein also referred to as sequencing adaptors), and barcodes can be attached to exposed nucleic acid ends. In some cases, oligonucleotides are attached iteratively to nucleic acid ends. Oligonucleotides comprising barcodes can be provided on an array as is taught in, for example, PCT Application No PCT/US2014/069642, which published as PCT Publication No. WO/2015/089243 on Jun. 18, 2015, and which is hereby incorporated by reference in its entirety.

Various methods for attaching oligonucleotides are available, including but not limited to hybridization, ligation, and double-stranded break repair. In some cases, the oligonucleotides are attached by hybridization. In some cases, the oligonucleotides are attached by ligation. In some cases, the oligonucleotides are attached by double-stranded break repair.

Oligonucleotides can be attached by hybridization, for example if both oligonucleotides and nucleic acid ends comprise sticky ends, or ends comprising overhangs, that are complementary in sequence. Under appropriate conditions, a sticky end of an oligonucleotide can hybridize to a sticky end of a nucleic acid end and attach the oligonucleotide non-covalently to the nucleic acid end.

Ligation of tags can be accomplished by enzymatic and non-enzymatic protocols. Examples of ligation reactions that are non-enzymatic can include the non-enzymatic ligation techniques described in U.S. Pat. No. 5,780,613, which is herein incorporated by reference in its entirety, and in U.S. Pat. No. 5,476,930, which is herein incorporated by reference in its entirety. Enzymatic ligation reactions can comprise use of a ligase enzyme. Non-limiting examples of ligase enzymes are ATP-dependent double-stranded polynucleotide ligases, NAD+ dependent DNA or RNA ligases, and single-strand polynucleotide ligases. Non-limiting examples of ligases are *Escherichia coli* DNA ligase, *Thermus filiformis* DNA ligase, Tth DNA ligase, *Thermus scotoductus* DNA ligase (I and II), T3 DNA ligase, T4 DNA ligase, T4 RNA ligase, T7 DNA ligase, Taq ligase, Ampligase (Epicentre®Technologies Corp.), VanC-type ligase, 9° N DNA Ligase, Tsp DNA ligase, DNA ligase I, DNA ligase III, DNA ligase IV, Sso7-T3 DNA ligase, Sso7-T4 DNA ligase, Sso7-T7 DNA ligase, Sso7-Taq DNA ligase, Sso7-*E. coli* DNA ligase, Sso7-Ampligase DNA ligase, and thermostable ligases. Ligase enzymes may be wild-type, mutant isoforms, and genetically engineered variants. Ligation reactions can contain a buffer component, small molecule ligation enhancers, and other reaction components.

Oligonucleotides can be attached with variable efficiency. An oligonucleotide can be attached with an efficiency of at least 10%, 20%, 30%, 40%, 50%, 60%, 65%, 70%, 75%, 80%, 85%, 90%, or 95% or greater. In some cases where multiple oligonucleotides are attached to a nucleic acid end, each oligonucleotide can be attached with variable efficiency. A first oligonucleotide can be attached to a nucleic acid end at an efficiency of at least 10% (e.g. at least 20%, 30%, 40%, 50%, 60%, 65%, 70%, 75%, 80%, 85%, 90%, or 95% or greater). A second oligonucleotide can be attached at an efficiency of at least 10% (e.g. at least 20%, 30%, 40%, 50%, 60%, 65%, 70%, 75%, 80%, 85%, 90%, or 95% or greater). Additional oligonucleotides can be attached to a nucleic acid end each with an efficiency of at least 10% (e.g. at least 20%, 30%, 40%, 50%, 60%, 65%, 70%, 75%, 80%, 85%, 90%, or 95% or greater). The resulting efficiency of attaching all oligonucleotides can be at least 10% (e.g. at least 20%, 30%, 40%, 50%, 60%, 65%, 70%, 75%, 80%, 85%, 90%, or 95% or greater).

Adapters

As used herein, the terms "adapter," "adaptor," and "adapter oligonucleotide" generally refer to any oligonucleotide having a sequence, at least a portion of which is known and can be joined to a target polynucleotide. In some cases, adapters are joined to a target polynucleotide by hybridization. In some cases, adapters are joined to a target polynucleotide by ligation. In some cases, adaptor oligonucleotides comprise DNA, RNA, nucleotide analogues, non-canonical nucleotides, labeled nucleotides, modified nucleotides, or combinations thereof. In certain cases, adaptor oligonucleotides are single-stranded, double-stranded, or partial duplex. In many cases, a partial-duplex adapter comprises one or more single-stranded regions and one or more double-stranded regions. In some cases, double-stranded adapters comprise two separate oligonucleotides hybridized to one another (also referred to as an "oligonucleotide duplex"). In further examples, the hybridization leaves one or more blunt ends, one or more 3' overhangs, one or more 5' overhangs, one or more bulges resulting from mismatched and/or unpaired nucleotides, or any combination of these. In some embodiments, a single-stranded adapter comprises two or more sequences that are able to hybridize with one another. When two such hybridizable sequences are contained in a single-stranded adapter, hybridization yields a hairpin structure (hairpin adapter). When two hybridized regions of an adapter are separated from one another by a non-hybridized region, a "bubble" structure results. In various cases, adaptors adopt a bubble structure comprising a single adapter oligonucleotide that comprises internal hybridizations, or comprise two or more adapter oligonucleotides hybridized to one another. In certain cases, internal sequence hybridization, such as between two hybridizable sequences in an adapter, produce a double-stranded structure in a single-stranded adapter oligonucleotide.

Some adapters contain one or more of a variety of sequence elements, including but not limited to, one or more amplification primer annealing sequences or complements thereof, one or more sequencing primer annealing sequences or complements thereof, one or more barcode sequences, one or more common sequences shared among multiple different adapters or subsets of different adapters, one or more restriction enzyme recognition sites, one or more overhangs complementary to one or more target polynucleotide overhangs, one or more probe binding sites (e.g. for attachment to a sequencing platform, such as a flow cell for massive parallel sequencing), one or more random or near-random sequences (e.g. one or more nucleotides selected at random from a set of two or more different nucleotides at one or more positions, with each of the different nucleotides selected at one or more positions represented in a pool of adapters comprising the random sequence), and combinations thereof. Two or more sequence elements may be non-adjacent to one another (e.g. separated by one or more nucleotides), adjacent to one another, partially overlapping, or completely overlapping. An amplification primer annealing sequence may also serve as a sequencing primer annealing sequence. Sequence elements can be located at or near the 3' end, at or near the 5' end, or in the interior of the adapter oligonucleotide. In some cases, for example, when an adapter oligonucleotide can form secondary structure, such as a hairpin, sequence elements are located partially or completely outside the secondary structure, partially or completely inside the secondary structure, or in between sequences participating in the secondary structure. In some cases, for example, when an adapter oligonucleotide comprises a hairpin structure, sequence elements are located partially or completely inside or outside the hybridizable sequences (the "stem"), including in the sequence between the hybridizable sequences (the "loop"). A difference in sequence elements can be any such that at least a portion of different adapters do not completely align, for example, due to changes in sequence length, deletion or insertion of one or more nucleotides, or a change in the nucleotide composition at one or more nucleotide positions (such as a base change or base modification).

Some adapter oligonucleotides comprise a 5' overhang, a 3' overhang, or both that is complementary to one or more target polynucleotides. The complementary overhangs are of various suitable lengths. In some cases, the various overhangs are one or more nucleotides in length, including but not limited to 1, 2, 3, 4, 5, 6, 7, 8, 9, 10, 11, 12, 13, 14, 15 bases in length or longer. In some cases, the complementary overhangs are about 1, 2, 3, 4, 5 or 6 bases in length. The complementary overhangs can comprise a fixed sequence. The complementary overhangs comprise a random sequence of one or more bases, such that one or more bases can be selected at random from a set of two or more different bases at one or more positions, with each of the different bases selected at one or more positions represented in a pool of adapters with complementary overhangs comprising the random sequence. The overhang are complementary to a target polynucleotide overhang produced by restriction endonuclease digestion in some cases. An adapter is joined to a target polynucleotide at the 3' end of the target polynucleotide in some cases. An adapter is joined to a target polynucleotide at the 5' end of the target polynucleotide in some cases. More than one adapter is joined to a polynucleotide in many cases, often sequentially.

Adapter oligonucleotides have a number of suitable lengths consistent with the disclosure herein, at least sufficient to accommodate the one or more sequence elements of which they are comprised. In some cases, adapters are at least 10, 15, 20, 25, 30, 35, 40, 45, 50, 55, 60, 65, 70, 75, 80, 90, 100, or 200 nucleotides in length or longer. In some cases, the adaptors are about 10 to about 50 nucleotides in length. In further examples, the adapters are about 20 to about 40 nucleotides in length.

Barcodes

The term "barcode," "tag," and "molecular tag" are used interchangeably in some cases herein. As used herein, they refer to a known nucleic acid sequence that allows some feature of a polynucleotide with which the barcode is associated to be identified. Barcodes are attached in a reversible or irreversible manner to polynucleotides for identification in various cases. In some cases, barcodes are attached by hybridization. In some cases, barcodes are attached by ligation. In some cases, the barcode sequence is located at a specific position on a larger polynucleotide sequence, e.g., an adapter oligonucleotide. In some cases, one barcode is used. In some cases, more than one barcode is used. Barcodes can each have a length within a range of 5 to 35 nucleotides, 6 to 30 nucleotides, or 8 to 20 nucleotides. In some cases, barcodes are at least 3, 4, 5, 6, 7, 8, 9, 10, 11, 12, 13, 14, or 15 nucleotides in length or longer. In some cases, barcodes can be shorter than 10, 9, 8, 7, 6, 5, or 4 nucleotides in length. In some cases, barcodes associated with some polynucleotides are a different length than barcodes associated with other polynucleotides. In some cases, the barcodes are selected from a group comprising at least 1, 2, 3, 4, 5, 6, 7, 8, 9, 10, 11, 12, 13, 14, 15, 20, 25, 50, 75, 100, 150, 200, 250, 300, 350, 400, 450, or 500 members or more. In some cases, a first, second and third barcode are selected from three groups, each comprising 8 members. In some cases, a first, second, and third barcode are selected from three groups, each comprising 96 members.

The melting temperatures of barcodes within a set can be within 10° C. of one another, within 5° C. of one another, or within 2° C. of one another. Barcodes can be members of a minimally cross-hybridizing set. For example, the nucleotide sequence of each member of such a set can be sufficiently different from that of every other member of the set such that no member can form a stable duplex with the complement of any other member under moderate or stringent hybridization conditions. The nucleotide sequence of each member of a minimally cross-hybridizing set can differ from those of every other member by at least two nucleotides.

In some cases, barcodes are of sufficient length and comprise sufficient sequence diversity to allow the differentiation and identification of samples based on the barcode or barcodes with which they are associated. In some cases, more than one barcode is used. Each barcode in a plurality of barcodes may differ from every other barcode in the plurality in at least two nucleotide positions, such as in at least 2, 3, 4, 5, 6, 7, 8, 9, 10 positions or more. Each barcode may differ from every other barcode in at least 2, 3, 4 or 5 positions or more. In some cases where more than one barcode is used, the combinations of barcodes are used to uniquely identify a polynucleotide associated with the barcode combination. In some cases, the barcode sequence is located on a larger polynucleotide sequence, e.g., an adapter oligonucleotide Sequencing Suitable sequencing methods described herein or otherwise known in the art can be used to obtain sequence information from nucleic acid molecules. Sequencing can be accomplished through classic Sanger sequencing methods. Sequence can also be accomplished using high-throughput next-generation sequencing systems. Non-limiting examples of next-generation sequencing methods include single-molecule real-time sequencing, ion semiconductor sequencing, pyrosequencing, sequencing by synthesis, sequencing by ligation, and chain termination.

Sequencing data can be used in methods of genome assembly and haplotype phasing as taught in the art, for example in PCT application no. PCT/US2014/014184, which published as PCT Publication No. WO/2014/121091, and which is incorporated herein by reference in its entirety).

Methods for Generating Labeled Nucleic Acid Segments

Phasing nucleic acid molecules, including but not limited to nucleic acid molecules separated in a genome is improved by incorporating long range interaction data obtained by linking together distant nucleic acid sequences. Methods herein contemplate the formation of linkages between distant nucleic acids sequences by binding nucleic acids, for example via cross-linking, to form nucleic acid complexes. In some cases, nucleic acid complexes comprise nucleic acids bound to association molecules comprising proteins such as nucleic acid binding proteins, for example histones, transcription factors, and transposases; non-protein organic molecules such as positively charged molecules; and nanoparticles. Following cross-linking, nucleic acids are treated, for example chemically, enzymatically, and/or mechanically by sonication, shearing, specific endonuclease treatment, non-specific endonuclease treatment, and/or enzymatic cleavage to expose internal nucleic acid ends. Treating nucleic acids to expose internal nucleic acid ends can result in the formation at least two fragments or segments derived from a single nucleic acid. The at least two fragments or segments remain associated with one another as the segments are bound together, for example in nucleic acid complexes, even though one or more physical linkages between segments, such as via their phosphodiester backbones, have been removed. The nucleic acid ends are tagged, for example by attaching a plurality of oligonucleotide labels comprising barcodes. In many cases, nucleic acid ends of the same nucleic acid complex are attached to barcodes comprising a common barcode sequence. To distinguish nucleic acid segments in a first cross-linked nucleic acid from nucleic acid segments in a second cross-linked nucleic acid, all of which share a first barcode sequence, additional barcodes (e.g. second barcodes, third barcodes, fourth barcodes, etc) with different barcode sequences can be attached iteratively to the nucleic acid segments of each of the first and second cross-linked nucleic acids. In some cases, the first cross-linked nucleic acid is attached to a second barcode that has a barcode sequence different from a barcode sequence of a second barcode attached to the second cross-linked nucleic acid. Barcode combinations comprising a common first barcode and a unique second barcode can be used to identify nucleic acid segments from the first cross-linked nucleic acid and the second cross-linked nucleic acid. As the number of nucleic acids to be identified increases, the number of barcode combinations can be increased accordingly to provide unique identification for each nucleic acid.

The number of barcode combinations can be increased by increasing the number of barcodes that are iteratively attached and/or increasing the number of barcode members in each iteration of attachment. For example, three iterations of barcode attachment with 3 barcode members in each iteration can result in $3^3=27$ barcode combinations. Increasing the number of members to 4 can increase the number of barcode combinations to $4^3=64$. Increasing the number of barcode members and iterations to 4 can increase the number of barcode combinations to $4^4=256$. Barcode lengths can be adjusted to provide unique barcode members for each iteration. For example, a barcode that is 1 base in length can have 4 members (A, T, C, and G) as there are four nucleotide choices in the standard DNA code diction, though this number can be increased by inclusion of non-canonical DNA bases such as dU, dI or other natural or unnatural base alternatives. Relying upon the canonical four bases, barcodes that are 2 bases in length can have $4^2=16$ unique members (AA, AT, AG, AC, TA, TT, TG, TC, GA, GT, GG, GC, CA, CT, CG, and CC). If a barcode is increased to 3 bases in length, there are $4^3=64$ possible unique members. The number of barcode members and iterations of barcode attachment can be selected and optimized without limitation to provide the desired number of barcode combinations.

Barcode labeled nucleic acid molecule segments can be sequenced to generate sequence reads, and barcode combinations can be used to infer the linkage relationships. Read-sets comprising sequence reads can be used to assemble nucleic acid molecules into contigs and scaffolds and to phase nucleic acid molecules.

In some cases, a method for labeling a first nucleic acid molecule and generating a first read-set comprises binding the first nucleic acid molecule (e.g. DNA, RNA, etc) comprising a first nucleic acid segment and a second nucleic acid segment. In some cases, the first nucleic acid molecule is DNA. The first nucleic acid molecule can be bound outside of a cell or inside of a cell. Binding can be reversible or non-reversible. In some cases, binding comprises cross-linking. In some cases, cross-linking comprises use of a cross-linking agent such as psoralen or UV light. In some cases, binding comprises use of a fixative agent, such as a fixative agent comprising formaldehyde. The first nucleic acid molecule can be bound to a first plurality of association molecules comprising amino acids, for example proteins and polypeptides; non-protein organic molecules; and nanoparticles. In some cases, association molecules comprise peptides and proteins such as DNA binding proteins, including but not limited to chromatin constituents such as histones, transcription factors, and transposases. In some cases, association molecules comprise non-protein organic molecules such as protamine, spermine, spermidine or other positively charged molecules. In some cases, association molecules comprise nanoparticles, such as positively charged nanoparticles including but not limited to platinum-based nanoparticles, magnetic-based nanoparticles, positively charged nanoparticles, amine-coated nanoparticles, gold-containing nanoparticles, silver-containing nanoparticles, DNA intercalators and any derivatives thereof, copper-containing nanoparticles, and combinations thereof. In some cases, binding a plurality of nucleic acid molecules to a plurality of association molecules comprises cross-linking. Cross-linking can comprise use of a cross-linking agents, such as cross-linking agents comprising formaldehyde, psoralen, UV light, mitomycin C, nitrogen mustard, melphalan, 1,3-butadiene diepoxide, cis diaminedichloroplatinum(II), and cyclophosphamide.

The plurality of complexes can be treated such that the first nucleic acid segment and the second nucleic acid segment are not joined by a phosphodiester bond, such as by severing. Severing the nucleic acid molecule can be achieved by various protocols, including but not limited to chemical, enzymatic, and mechanical protocols including shearing, sonication, nonspecific endonuclease treatment, specific endonuclease treatment, and enzymatic cleavage. In some cases, a restriction endonuclease is used for nonspecific or specific endonuclease treatment.

The plurality of nucleic acid segments can comprise nucleic acid ends to which oligonucleotides are attached. Oligonucleotides (e.g. DNA oligonucleotides and/or RNA oligonucleotides) can comprise labels, tags, adaptors, sequencing adaptors, and barcodes. In some cases, the oligonucleotides comprise barcodes or barcode nucleic acids. The first nucleic acid segment and the second nucleic acid segment are labelled with oligonucleotides comprising barcode nucleic acids. Two or more barcode nucleic acids can be attached via an iterative process. In some cases, the first nucleic acid segment and the second nucleic acid segment are labeled using a first nucleic acid barcode, a second nucleic acid barcode, and a third nucleic acid barcode. In some cases, the first barcode nucleic acid and the second barcode nucleic acid are non-identical. In some cases, the third nucleic acid barcode is non-identical to the first barcode nucleic acid and the second barcode nucleic acid. In some cases, the barcodes are attached by hybridization. In some cases, the barcodes are attached by ligation. In some cases, the barcodes are attached covalently.

The labeled nucleic acid segments are sequenced and used to generate a first read-set. A first read-set can be generated by associating the first nucleic acid segment and the second nucleic acid segment using the first barcode nucleic acid and the second barcode nucleic acid. In some cases, a first contig having the first nucleic acid segment and a second contig having the second nucleic acid segment can be assembled into a single scaffold. In some cases, the first nucleic acid segment and the second nucleic acid segment are assigned to a common phase.

In some cases, the first nucleic acid molecule comprises a third nucleic acid segment labelled with the first barcode nucleic acid and the second barcode nucleic acid. The third nucleic acid can be sequenced and a first read-set can comprise a sequence of the third nucleic acid segment. In some cases, the method comprises binding, such as by cross-linking, a second nucleic acid molecule to a plurality of association molecules outside of a cell and thereby generating a second complex, wherein the second nucleic acid molecule comprises a third nucleic acid segment and a fourth nucleic acid segment; treating the second complex such that the third nucleic acid segment and the fourth nucleic acid segment are not joined by a phosphodiester bond; labelling each of the third nucleic acid segment and the fourth nucleic acid segment with the first barcode nucleic acid; separating the first complex from the second complex; labelling each of the third nucleic acid segment and the fourth nucleic acid segment with a third barcode nucleic acid; and sequencing the third nucleic acid segment and the fourth nucleic acid segment thereby obtaining a second read-set. In some cases, a plurality of contigs from the second nucleic acid molecule is used to assemble a second read-set. In some cases, the first read-set and the second read-set are used to determine the phase of the first nucleic acid molecule and the second nucleic acid molecule.

In some cases, a plurality of nucleic acid molecules is labeled. A method of labeling a plurality of nucleic acid molecules can comprise binding a plurality of nucleic acid molecules to a plurality of nucleic acid binding moieties to form a plurality of nucleic acid complexes. In some cases, binding comprises cross-linking. The plurality of nucleic acid complexes can be cleaved such that phosphodiester backbones are cleaved to expose nucleic acid ends. Cleaving can be accomplished by various protocols, including sonicating, shearing, nonspecific endonuclease digestion, specific endonuclease digestion and enzymatic cleavage. In some cases, the plurality of nucleic acid complexes are tagged such that a first complex is tagged by a first nucleic acid tag having a first sequence and a second complex is tagged by a first nucleic acid tag having a second sequence. In some cases, the plurality of nucleic acid complexes are tagged such that the first complex is tagged using a second nucleic acid tag. In some cases, the first complex is tagged using at least one additional nucleic acid tag, for example a third nucleic acid tag and a fourth nucleic acid tag. Nucleic acid tags can be attached by various methods, for example by hybridization, ligation, and double-stranded break repair.

Labeled nucleic acids of the complexes are sequenced to obtain a plurality of reads. In some cases, the plurality of reads comprises a read comprising a second tag sequence, a first tag sequence and a first nucleic acid molecule sequence adjacent to the first tag sequence, and a read comprising a second tag sequence, a first tag sequence and a second nucleic acid molecule sequence adjacent to the first tag sequence. In some cases, a nucleic acid molecule sequence of a nucleic acid complex is sequenced such that a second tag, a first tag and a nucleic acid molecule sequence adjacent to the first tag are obtained in a single read. In some cases, the plurality of reads comprises a read comprising sequences of all tags and a first nucleic acid molecule sequence adjacent to the first tag sequence, and a read comprising sequences of all tags and a second nucleic acid molecule sequence adjacent to the first tag sequence. In some cases, a nucleic acid molecule sequence of a nucleic acid complex is sequenced such that all tag sequences and a nucleic acid molecule sequence adjacent to the first tag are obtained in a single read. In some cases, a shared combination of the first tag, the second tag, and the third tag among a first read and a second read from a plurality of reads can indicate that a first nucleic acid molecule sequence and a second nucleic acid molecule sequence are segments derived from a single nucleic acid molecule. A shared combination of the first tag, the second tag, and the third tag may indicate that the first nucleic acid molecule and the second nucleic acid molecule are derived from the same cross-linked nucleic acid complex, sharing a common barcode combination resulting from ligation with the same series of tags. In some cases, a combination of the first tag, the second tag, and the third tag that is different among a first read and a second read from a plurality of reads can indicate that a first nucleic acid molecule sequence and a second nucleic acid molecule sequence are not derived from a single nucleic acid molecule. In some cases, the plurality of reads comprises a read comprising a fourth tag sequence, a third tag sequence, a second tag sequence, a first tag sequence and a first nucleic acid molecule sequence adjacent to the first tag sequence, and a read comprising a fourth tag sequence, a third tag sequence, a second tag sequence, a first tag sequence and a second nucleic acid molecule sequence adjacent to the first tag sequence. In some cases, a nucleic acid molecule sequence of a nucleic acid complex is sequenced such that a fourth tag, a third tag, a second tag, a first tag and a nucleic acid molecule sequence adjacent to the first tag are obtained in a single read. In some cases, a shared combination of the first tag, the second tag, the third tag, and the fourth tag among a first read and a second read from a plurality of reads can indicate that a first nucleic acid molecule sequence and a second nucleic acid molecule sequence are segments derived from a single nucleic acid molecule. A shared combination of the first tag, the second tag, the third tag, and the fourth tag may indicate that the first nucleic acid molecule and the second nucleic acid molecule are derived from the same cross-linked nucleic acid complex, sharing a common barcode combination resulting from ligation with the same series of tags. In some cases, a combination of the first tag, the second tag, the third tag, and the fourth tag that is different among a first read and a second read from a plurality of reads can indicate that a first nucleic acid molecule sequence and a second nucleic acid molecule sequence are not derived from a single nucleic acid molecule. In some cases, the plurality of reads comprises a read comprising one or more tag sequences and a first nucleic acid molecule sequence adjacent to a first tag sequence, and a read comprising one or more tag sequences and a second nucleic acid molecule sequence adjacent to a first tag sequence. In some cases, a nucleic acid molecule sequence of a nucleic acid complex is sequenced such that one or more tag sequences and a nucleic acid molecule sequence adjacent to a first tag are obtained in a single read.

Nucleic acid molecule sequences sharing common tag sequences can map to a common phase. In some cases, a first nucleic acid molecule sequence and a second nucleic acid molecule sequence are assigned to a common phase if the first nucleic acid molecule sequence read and the second nucleic acid molecule sequence read share common tag sequences, for example a common second tag sequence and a common first tag sequence. In some cases, a first nucleic acid molecule sequence and a second nucleic acid molecule sequence are assigned to a common phase if the first nucleic acid molecule sequence read and the second nucleic acid molecule sequence read share a common third tag sequence, a common second tag sequence and a common first tag sequence. In some cases, a first nucleic acid molecule sequence and a second nucleic acid molecule sequence are assigned to a common phase if the first nucleic acid molecule sequence read and the second nucleic acid molecule sequence read share a common fourth tag sequence, a common third tag sequence, a common second tag sequence and a common first tag sequence. In some cases, the nucleic acid molecules with nucleic acid molecule sequence reads sharing common tag sequences are mapped to a common phase. In some cases, a common third tag sequence is shared. In some cases, the nucleic acid sequences are assigned to a phase comprising at least one other nucleic acid sequence. In some cases, at least 50%, 60%, 65%, 70%, 75%, 80%, 85%, 90%, 95% or more of the nucleic acid sequences are assigned to a phase comprising at least one other nucleic acid sequence. In some cases, the first nucleic acid molecule sequence and the second nucleic acid molecule sequence assigned to a common phase are separated in a genome. The first nucleic acid molecule sequence and second nucleic acid molecule sequence assigned to a common phase can be separated by at least 250 bases, 500 bases, 750 bases, 1 kilobase (kb), 2 kb, 3 kb, 4 kb, 5 kb, 6 kb, 7 kb, 8 kb, 9 kb, 10 kb, 15 kb, 20 kb, 30 kb, 40 kb, 50 kb, 60 kb, 70 kb, 80 kb, 90 kb, 100 kb, 125 kb, 150 kb or more in a genome. In some cases, optimization of cross-linking conditions, digestion conditions, and tag attachment conditions can generate phased sequence reads that are separated in a genome, for example, by at least 10 kb or more. In some cases, a first nucleic acid molecule sequence and a second nucleic acid molecule sequence are assigned to a separate phase if the first nucleic acid molecule sequence read and the second nucleic acid molecule sequence read do not share common tag sequences, such as a common second tag sequence and a common first tag sequence. In some cases, a first nucleic acid molecule sequence and a second nucleic acid molecule sequence are assigned to a separate phase if the first nucleic acid molecule sequence read and the second nucleic acid molecule sequence read do not share a common third tag sequence, a common second tag sequence and a common first tag sequence. In some cases, a first nucleic acid molecule sequence and a second nucleic acid molecule sequence are assigned to a separate phase if the first nucleic acid molecule sequence read and the second nucleic acid molecule sequence read do not share a common fourth tag sequence, a common third tag sequence, a common second tag sequence and a common first tag sequence. In some cases, a first tag and a second tag are identical but a third tag sequence is not shared, indicating that the reads do not map to a common molecule of origin.

In some cases, nucleic acid sequences are assigned to contigs. In some cases, at least 50%, 60%, 65%, 70%, 75%, 80%, 85%, 90%, 95% or more of the nucleic acid sequences are assigned to a contig comprising at least one other nucleic acid sequence.

Nucleic acid molecules sharing common tag sequences, for example a common second tag sequence and a common first tag sequence, can map to a common scaffold. In some cases, nucleic acid molecules share a common third tag sequence and map to a common scaffold. In some cases, a first nucleic acid molecule sequence and a second nucleic acid molecule sequence are assigned to a common scaffold if the first nucleic acid molecule sequence read and the second nucleic acid molecule sequence read share a common second tag sequence and a common first tag sequence. In some cases, a first nucleic acid molecule sequence and a second nucleic acid molecule sequence are assigned to a common scaffold if the first nucleic acid molecule sequence read and the second nucleic acid molecule sequence read share a common third tag sequence, a common second tag sequence and a common first tag sequence. In some cases, a first nucleic acid molecule sequence and a second nucleic acid molecule sequence are assigned to a common scaffold if the first nucleic acid molecule sequence read and the second nucleic acid molecule sequence read share a common fourth tag sequence, a common third tag sequence, a common second tag sequence and a common first tag sequence. In some cases, the nucleic acid molecules with nucleic acid molecule sequence reads sharing common tag sequences are mapped to a common scaffold. In some cases, the nucleic acid sequences are assigned to a scaffold comprising at least one other nucleic acid sequence. In some cases, the assignment is made for at least 50%, 60%, 65%, 70%, 75%, 80%, 85%, 90%, or 95% of the nucleic acid sequences. In some cases, the first nucleic acid molecule sequence and the second nucleic acid molecule sequence assigned to a common scaffold are separated in a genome. In some cases, the first and second nucleic acid molecule sequence assigned to a common scaffold are separated by at least 250 bases, 500 bases, 750 bases, 1 kilobase (kb), 2 kb, 3 kb, 4 kb, 5 kb, 6 kb, 7 kb, 8 kb, 9 kb, 10 kb, 15 kb, 20 kb, 30 kb, 40 kb, 50 kb, 60 kb, 70 kb, 80 kb, 90 kb, 100 kb, 125 kb, 150 kb or more in a genome. In some cases, a first nucleic acid molecule sequence and a second nucleic acid molecule sequence are assigned to distinct scaffolds if the first nucleic acid molecule sequence read and the second nucleic acid molecule sequence read share common tag sequences, such as a common second tag sequence and a common first tag sequence.

Also disclosed herein are methods for labeling a plurality of nucleic acid molecules which can be used for assembling and phasing a plurality of contigs. In some cases, the method comprises binding a plurality of nucleic acid molecules to a plurality of association molecules to form a plurality of nucleic acid complexes, wherein the plurality of nucleic acid molecules comprises a first nucleic acid molecule. In some cases, association molecules comprise polypeptides; non-protein organic molecules; and nanoparticles. In some cases, association molecules comprise peptides and proteins such as DNA binding proteins, including but not limited to chromatin constituents such as histones, transcription factors, and transposases. In some cases, association molecules comprise non-protein organic molecules such as protamine, spermine, spermidine or other positively charged molecules. In some cases, association molecules comprise nanoparticles, such as positively charged nanoparticles including but not limited to platinum-based nanoparticles, magnetic-based nanoparticles, positively charged nanoparticles, amine-coated nanoparticles, gold-containing nanoparticles, silver-containing nanoparticles, DNA intercalators and any derivatives thereof, copper-containing nanoparticles, and combinations thereof. In some cases, binding a plurality of nucleic acid molecules to a plurality of association molecules comprises cross-linking. Cross-linking can comprise use of a cross-linking agents, such as cross-linking agents comprising formaldehyde, psoralen, UV light, mitomycin C, nitrogen mustard, melphalan, 1,3-butadiene diepoxide, cis diaminedichloroplatinum(II), and cyclophosphamide.

The plurality of complexes can be severed such that phosphodiester backbones are cleaved to generate a plurality of nucleic acid segments and expose internal nucleic acid ends. Severing the nucleic acid molecule can comprise various methods, including but not limited to chemical, enzymatic, and mechanical protocols such as shearing, sonication, nonspecific endonuclease treatment, specific endonuclease treatment, and enzymatic cleavage. In some cases, severing comprises digesting by contact with a restriction endonuclease.

The plurality of nucleic acid segments can comprise nucleic acid ends to which oligonucleotides are attached. Oligonucleotides (e.g. DNA oligonucleotides and/or RNA oligonucleotides) can comprise labels, tags, adaptors, sequencing adaptors, and barcodes. In some cases, the oligonucleotides, for example oligonucleotides comprising barcodes, are attached to nucleic acid segments via an iterative process to generate multiply labeled nucleic acid segments. The additional tags are attached via an iterative process comprising (i) attaching a barcode nucleic acid to the nucleic acid segments; (ii) separating the first complex from a plurality of other complexes; and (iii) repeating (i) and (ii) one or more times. The barcodes can be attached by various methods, including but not limited to hybridization, ligation, and double-stranded break repair.

The multiply labeled nucleic acid segments can be sequenced and used to generate read-sets. In some cases, contigs are assembled using the read-pairs. In some cases, read-sets are used to determine the contigs that originate from the first nucleic acid molecule and thereby phase the first nucleic acid molecule. In some cases, read-sets are generated by binning the labeled nucleic acid segments that comprise a same label. In some cases, at least 1% of the labeled nucleic acid segments in the read-set span a distance of at least 5 kb, 10 kb, 15 kb, 20 kb, 25 kb, 30 kb, 35 kb, 40 kb, 45 kb, 50 kb, 55 kb, 60 kb, 65 kb, 70 kb, 75 kb or greater on the first nucleic acid molecule. In some cases, at least 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 2%, 3%, 4%, 5% or more of the labeled nucleic acid segments in the read-set span a distance of at least 5 kb, 10 kb, 15 kb, 20 kb, 25 kb, 30 kb, 35 kb, 40 kb, 45 kb, 50 kb, 55 kb, 60 kb, 65 kb, 70 kb, 75 kb or greater on the first nucleic acid molecule. In some cases, the phasing is performed at least 45%, 50%, 55%, 60%, 65%, 70%, 75%, 80%, 85%, 86%, 87%, 88%, 89%, 90%, 91%, 92%, 93%, 94%, or 95% accuracy or greater.

Tag information does not in all cases strictly correspond to phase information, but is informative as to phase information. Generally referring to the disclosure above, the presence of a common tag pattern on a pair of sequence reads indicates that the reads either 1) originated from a common molecule, or 2) are shared in common by chance.

In most cases, common tagging will not arise by chance, and thus most common tagged sequences, particularly commonly tagged sequences that are independently mapped to a common contig, are safely inferred to map to a common phase of that contig, that is, to the same haploid molecule of a diploid organism. Groups of reads that map together to a single or a few contigs suspected of being adjacent and that share a tag sequence are likely to be in phase on a single molecule. Groups of reads that share a common tag sequence but that map to contigs suspected to be on separate chromosomes, for example, are more likely to have obtained their common tag sequences by chance. Multiple instances of sequence clusters sharing the exact tag sequence but mapping to two separate contigs or suspected chromosomes, however, may indicate that a translocation has occurred by which a fragment of one chromosome has become attached to a second, such that the reads are in fact in phase on the chromosome that is the result of the translocation.

The presence of a non-identical tag pattern among a pair of sequence reads indicates that the sequences did not arise from a common molecule immediately prior to tagging. However, if multiple identical or overlapping copies of a nucleic acid molecule exist in a single sample, then two sets of sequence reads can arise that differ in their tag patterns, indicating that they arose from different molecules in the sample, but that nonetheless map to the same in phase chromosome in a diploid cell. That is, tag pattern information is indicative as to whether sequences arose from a common molecule, and in general, tag pattern information correlates to phase information. However, as discussed above, in discrepancies, tag pattern information is more properly indicative of a common molecule of origin. In cases where molecule of origin and nucleic acid phase determinations show some discrepancy, one of skill in the art is able to resolve these discrepancies such that some phase information is nonetheless determinable from the tag pattern information generated through the methods herein.

The present disclosure also provides methods of packaging a nucleic acid sample into phase-tagged fragments. To package a nucleic acid sample into phase tagged-fragments, a constituent of the nucleic acid sample is bound, cleaved into segments, and iteratively tagged with tags, such that the combination of two or more tags can be used to determine phase information. In some cases, a method of packing a nucleic acid sample into phase-tagged fragments comprises the steps of (a) forming intramolecular phosphodiester backbone-independent bonds to bind a constituent of the nucleic acid sample; (b) cleaving the constituent of the nucleic acid sample to expose at least one pair of internal double-strand break ends; (c) tagging the at least one pair of internal double-strand break ends with a first tag set; (d) tagging the at least one pair of internal double-strand break ends with a second tag set; (e) tagging the at least one pair of internal double-strand break ends with a third tag set, wherein the presence of a non-identical first tag set, second tag set, and third tag set on a pair of molecules indicates that the pair of molecules originate from non-identical constituents of the nucleic acid sample.

In some cases, binding a constituent of a nucleic acid sample comprises cross-linking. Cross-linking comprises use of a cross-linking agent, such as cross-linking agents comprising formaldehyde, psoralen, UV light, mitomycin C, nitrogen mustard, melphalan, 1,3-butadiene diepoxide, cis diaminedichloroplatinum(II), and cyclophosphamide. In some cases, a constituent of the nucleic acid sample is bound to an association molecule such as association molecules comprising amino acids, for example polypeptides and proteins including nucleic acid binding proteins; non-protein organic molecules; and nanoparticles. In some cases, association molecules comprise peptides and proteins such as DNA binding proteins, including but not limited to chromatin constituents such as histones, transcription factors, and transposases. In some cases, association molecules comprise non-protein organic molecules such as protamine, spermine, spermidine or other positively charged molecules. In some cases, association molecules comprise nanoparticles, such as positively charged nanoparticles including but not limited to platinum-based nanoparticles, magnetic-based nanoparticles, positively charged nanoparticles, amine-coated nanoparticles, gold-containing nanoparticles, silver-containing nanoparticles, DNA intercalators and any derivatives thereof, copper-containing nanoparticles, and combinations thereof. The bound nucleic acid is then cleaved using any method of cleavage as previously disclosed herein to expose at least one pair of internal double-strand break ends. In some cases, cleavage comprises digestion by contacting with a restriction endonuclease. At least one pair of internal double-strand break ends can be tagged with a first tag set. A first tag set can be less than 15 bases (e.g. less than 10 bases) in length. In some cases, at least one pair of internal double-strand break ends is tagged with a second tag set. A second tag set can be less than 15 bases (e.g. less than 10 bases) in length. In some cases, at least one pair of internal double-strand break ends is tagged with a third tag set. A third tag set can be less than 15 bases (e.g. less than 10 bases) in length. In some cases, the method comprises tagging the at least one pair of internal double-strand break ends with a fourth tag set. In some cases, a method of tagging comprises ligating a tag to the at least one pair of internal double-strand break ends. In some cases, a method of tagging comprises hybridizing a tag to the at least one pair of internal double-strand break ends. In some cases, tagging comprises double-stranded break repair.

In one illustrative embodiment as shown in FIG. 1A, 1 ng of chromatin aggregates attached to a solid support of beads is split across 8 tubes, each containing 1 of 8 members of the first adapter group (first iteration) comprising double-stranded DNA (dsDNA) adapters to be ligated. Each of the 8 adapters can have the same 5' overhang sequence for ligation to the nucleic acid ends of the cross-linked chromatin aggregates, but otherwise has a unique dsDNA sequence. After the first adapter group is ligated, the cross-linked chromatin aggregates can be pooled back together and washed to remove the ligation reaction components. The scheme of distributing, ligating, and pooling can be repeated 2 additional times (2 iterations) with additional adapter groups as shown in FIG. 1A. Following ligation of members from each adapter group, a cross-linked chromatin aggregate can be ligated to multiple barcodes as shown in FIG. 1B. In some cases, the sequential ligation of a plurality of members of a plurality of adapter groups (iterations) results in barcode combinations.

The number of barcode combinations available depends on the number of members per iteration and the total number of barcode members used. For example, 3 iterations comprising 8 members each can have 83 possible combinations. In some cases, barcode combinations are unique. In some cases, barcode combinations are redundant. The total number of barcode combinations can be adjusted by increasing or decreasing the number of members and/or increasing or decreasing the number of attachment iterations. When more than one adapter group is used, a distributing, ligating, and pooling scheme can be used for iterative adapter ligation. In some cases, the scheme of distributing, ligating, and pooling can be repeated at least 3, 4, 5, 6, 7, 8, 9, or 10 additional times. In some cases, the members of the last adapter group include a sequence for subsequent enrichment of adapter-ligated DNA during sequencing library preparation through PCR amplification.

A sequencing library can be prepared from the adapter-labeled chromatin aggregates. In some cases, the resulting sequencing data is analyzed to determine 1) the efficiency of ligating a first adapter; and 2) the efficiency of the subsequent, sequential adapter ligations. In some cases, a majority of the barcodes are represented within a factor of 2 of the expected number of reads per barcode. In some cases, about 10% to 90% of the barcodes are represented within a factor of about 1.5 to 5 of the expected number of reads per barcode. In some cases, at least 10%, 20%, 30%, 40%, 50%, 60%, 70%, 80%, or 90% of the barcodes are represented within a factor of at least 1.5, 2, 2.5, 3, 3.5, 4, 4.5, or 5 of the expected number of reads per barcode. In some cases, about 65% of the barcodes are represented within a factor of about 2. The reagents and components for performing the above disclosed methods for labeling nucleic acids and assembling and phasing a plurality of contigs are provided in one or more kits. In some cases, a kit for performing the methods disclosed above comprises a plurality of association molecules or nucleic acid binding moieties, such as nucleic acid binding proteins, non-protein organic molecules, and nanoparticles; a fixative agent, such as, for example formaldehyde or psoralen; a restriction endonuclease; a ligase; one or more barcode nucleic acids or adapter oligonucleotides comprising barcodes; one or more sequencing primers; or a combination thereof The above disclosed methods for assembling and phasing a plurality of contigs are implemented on programmed and/or configured computer systems. In some cases, a computer system is programmed and/or configured for cross-linking, digesting, ligating, sequencing, generating read-sets, assigning read-sets to a common phase, assigning read-sets to a common scaffold, assigning read-sets to a distinct phase, assigning read-sets to a distinct scaffold, assigning read-sets to a common contig, or a combination thereof.

Compositions

Disclosed herein are compositions that can be used in methods herein, for example compositions that can be used for haplotype phasing or determination of molecule of origin for a tagged nucleic acid sequence. Compositions provided herein may comprise any of the elements for performing any of the methods of the present disclosure. In some cases, a composition that can be used for haplotype phasing comprises a first nucleic acid segment and a second nucleic acid segment. In some cases, each of a first nucleic acid segment and a second nucleic acid segment are bound to a plurality of association molecules to generate an in vitro complex, wherein each of the first nucleic acid segment and the second nucleic acid segment is attached to a first barcode nucleic acid, and wherein each of the first barcode nucleic acid is attached to a second barcode nucleic acid. In some cases, each of the second barcode nucleic acids is attached to a third barcode nucleic acid. Barcode nucleic acids can be attached by various methods, including but not limited to hybridization, ligation, and double-stranded break repair. In some cases, the first and second nucleic acid segments are bound to a plurality of association molecules by cross-linking. Cross-linking can comprise use of a fixative agent such as formaldehyde.

In some cases, a first nucleic acid segment and a second nucleic acid segment each originate from a first nucleic acid molecule. In some cases, the first nucleic acid segment and the second nucleic acid segment are at least 5, 10, 20, 30, 40, 50, 60, 70, 80, 85, 90, 95, 100, 125, 150, 200, 250, or 300 kb or farther apart on the first nucleic acid molecule.

In some cases, the in vitro complex is immobilized on a solid support. Non-limiting examples of a solid support are an array or microarray, a slide, a chip, a microwell, a column, a tube, a particle or a bead. In some cases, the solid support comprises a glass, metal, ceramic or polymeric material. In some cases, the solid support comprises a nucleic acid microarray (e.g., a DNA microarray). In some cases, the solid support comprises a particle (non-spherical) or sphere/bead. A particle or bead can be hollow or solid at the center.

In some cases, a particle or bead comprises polystyrene, ferromagnetic materials, silica, or combinations thereof. In some cases, a solid support comprises a polystyrene particle or bead, a magnetic particle or bead, a silica particle or bead, or combinations thereof, for example, e.g., a polystyrene magnetic bead. In some cases, a magnetic particle or bead comprises one or more magnetic cores with a coating matrix of polymers, siliceous oxide, silica or hydroxylapatite with functionalized groups. In some cases, a magnetic core comprises material with superparamagnetic or ferromagnetic properties, such as, for example, magnetite or maghemite. In some cases, a magnetic particle or bead comprises ferrite crystals dispersed in a suspension of styrene/divinylbenzene monomers.

In some cases, particles or beads have uniform diameters, wherein the diameter of a particle refers to the length of the longest linear distance formed between two points on the particle and the diameter of a sphere refers to the length of a line segment that passes through the center of the circle and whose endpoints lie on the sphere. In some cases, particles or beads have non-uniform diameters.

The diameter of a particle or bead can be on the order of nanometers (nm) or micrometers (μm). In some cases, the diameter of a particle or bead is at least 1, 5, 10, 15, 20, 25, 50, 75, 100, 150, 200, 250, 300, 350, 400, 450, 500, 600, 650, 700, 750, 800, 850, 900, 950, or 1000 nm in diameter or larger. In some cases, the diameter of a particle or bead is at least 1, 5, 10, 15, 20, 25, 50, 75, 100, 150, 200, 250, 300, 350, 400, 450, 500, 600, 650, 700, 750, 800, 850, 900, 950, or 1000 μm in diameter or larger.

In some cases, the beads are bound to an additional solid support such as a substrate. In some cases, the beads are reversibly bound to the additional solid support through interactions such as, but not limited to, electrostatic interactions and electric fields, hydrophobic interactions, magnetic interactions, and electromagnetic interactions. In some cases, the particles or beads are irreversibly bound to the additional solid support for example by the presence of a covalent bond.

In some cases, an in vitro complex is immobilized on a particle or bead at a one to one ratio. In some cases, there is less than one in vitro complex immobilized on a particle or bead. In some cases, there is more than one in vitro complex immobilized on a particle or bead. In some cases, there is at least 1, 2, 3, 4, 5, 6, 7, 8, 9, 10 or more in vitro complexes immobilized on a particle or bead.

Also disclosed herein are nucleic acid compositions from organisms. In some embodiments, a nucleic acid composition from an organism comprises a nucleic acid library. A nucleic acid composition from an organism comprising a nucleic acid library can be used for de novo genome assembly. In some cases, each library constituent comprises a nucleic acid comprising a nucleic acid sample segment, a first tag, a second tag, and a third tag. In some cases, a difference between a first library constituent and a second library constituent in any one of a first tag sequence, second tag sequence and third tag sequence independently indicates that the first library constituent and the second library constituent do not originate from a common nucleic acid molecule.

An organism can be a human or non-human animal, including mammals and non-mammals, vertebrates and invertebrates, and may also be any multicellular organism or single-celled organism such as a eukaryotic or prokaryotic organism, archaeon, microorganisms, and aquatic plankton. Non-limiting examples of organisms from which a nucleic acid comprising a nucleic acid segment can be obtained are plants, algae, animals, bacteria, archaea, fungi, protists, monerans, viruses, mitochondria, and chloroplasts. Non-limiting examples of animals are a cow, a pig, a mouse, a rat, a chicken, a cat, a dog, and a mammal, such as a human.

In some cases, a first tag, a second tag, and a third tag comprise barcodes. In some cases, a first tag, a second tag, and a third tag comprise barcodes between 1 base and 15 bases in length. In some cases, a first tag and a second tag are non-identical. In some cases, a first tag and a second tag are identical. In some cases, a third tag is non-identical to a first tag and a second tag.

In some cases, each library constituent is formed by attaching a first tag, a second tag, and a third tag to a nucleic acid sample segment. Various methods of attaching a tag are available, including but not limited to ligation and hybridization.

The reagents and components for compositions as disclosed herein can be provided in one or more kits. In some cases, a kit comprises a first nucleic acid segment; a second nucleic acid segment; a plurality of association molecules or nucleic acid binding moieties, such as nucleic acid binding proteins; a fixative agent, for example formaldehyde; a restriction endonuclease; a ligase; a solid support on which an in vitro complex can be immobilized, for example, a particle or a bead; one or more barcode nucleic acids or adapter oligonucleotides comprising barcodes; one or more sequencing primers; or a combination thereof.

In Vitro Libraries of Read-Sets

Disclosed herein are in vitro libraries consistent with the subject methods. In vitro libraries are used for genome analysis and haplotype phasing in some cases. In some embodiments, an in vitro library comprises a plurality of read-sets each comprising at least a first nucleic acid segment and a second nucleic acid segment. Read-sets can be generated using any of the methods of binding nucleic acids including cross-linking nucleic acids; cleaving nucleic acids; attaching barcodes to nucleic acid ends; sequencing labeled nucleic acid segments; and associating barcode combinations as described herein. In some cases, each of the first nucleic acid segment and the second nucleic acid segment are attached to a first barcode nucleic acid, and each of the first barcode nucleic acid is attached to a second barcode nucleic acid. In some cases, the second barcode nucleic acid is attached to at least one additional barcode nucleic acid. Barcodes can be attached by various methods, including but not limited to hybridization, ligation, and double-stranded break repair.

In some cases, a first nucleic acid segment and a second nucleic acid segment each originate from a first nucleic acid molecule. In some cases, the first nucleic acid segment and the second nucleic acid segment are at least 5, 10, 20, 30, 40, 50, 60, 70, 80, 85, 90, 95, 100, 125, 150, 200, 250, or 300 kb or farther apart on the first nucleic acid molecule. In some cases, at least 0.5%, 0.75%, 1%, 1.25%, 1.5%, 2%, 3%, 4%, 5%, 7.5%, 10%, 12.5%, 15% or more of the read-sets comprise a first nucleic acid segment and a second nucleic acid segment that are at least 10 kb (e.g. at least 25 kb, 50 kb, 75 kb, 100 kb, 200 kb, 300 kb or farther) apart on the single nucleic acid molecule.

Reagents and components for generating in vitro libraries of read-sets as disclosed above are provided in one or more kits. In some cases, a kit comprises at least a first nucleic acid segment; at least a second nucleic acid segment; a plurality of association molecules or nucleic acid binding moieties, such as proteins, for example histones for the formation of a nucleic acid complex; a fixative agent, such as, for example formaldehyde; a restriction endonuclease; a ligase; a solid support on which a nucleic acid complex can be immobilized, such as, for example, a particle or a bead; one or more barcode nucleic acids or adapter oligonucleotides comprising barcodes; one or more sequencing primers; or a combination thereof.

The above disclosed methods for generating in vitro libraries of read-sets are implemented on programmed and/or configured computer systems. In some cases, a computer system is programmed and/or configured for cross-linking, digesting, ligating, sequencing, generating read-sets, assigning read-sets to a common phase, assigning read-sets to a common scaffold, assigning read-sets to a distinct phase, assigning read-sets to a distinct scaffold, assigning read-sets to a common contig, or a combination thereof.

Modeling the Minimum Number of Barcodes Required and Maximum DNA Sampled

The minimum number of barcodes required is modeled using the following relationship that incorporates information about the input DNA and sequencing capacity:

$$b = \frac{fNL}{\epsilon G}, \text{ that is } b = (fNL/\epsilon G)$$

where b is the number of barcodes, N the total number of reads sequenced, f the rate of noise reads (the proportion of the N reads that do not cluster and are assumed to sample the genome independently and uniformly), L the length of the DNA molecule in one chromatin aggregate, G the length of DNA in one genome, and ε the probability that a noise read of the same barcode is present within a distance L of a read cluster. A high ε may be undesirable because of the higher incidence of inappropriate inclusion of noise reads in the cluster, which introduces confounding signal into variant phase inferences.

The maximum number of chromatin aggregates to sample can be represented by the amount of DNA sampled. This amount is determined with the following model that incorporates information about the input DNA, sequencing capacity, and the desired number of reads per aggregate:

$$m = \frac{(1-f)NL}{n}, \text{ that is, } m = ((1-f)NL)/n$$

where m is the amount of DNA to sample and n the number of reads per chromatin aggregate. The other parameters are the same as described for the minimum number of barcodes model previously described.

To calculate the amount of DNA to sample for haplotype phasing a human genome using in vitro chromatin aggregates that are assembled from DNA molecules which are on average 150 kb in length, the following parameters are used for the model: $G=3.2\times10^9$ ($3.45\times10^{-12}$ g) and $L=1.5\times10^5$ bp ($1.6\times10^{-16}$ g). The minimum number of barcodes required can be graphed as a function of probability (ε) of a noise read in a cluster for various noise rates (f) as shown in FIG. 2A. The minimum number of barcodes b can be selected to require ε<0.01 for various noise rates (f). Similarly, the maximum amount of DNA is determined using an average of 10 reads per chromatin aggregate (m) and various values of noise rate (f) as shown in FIG. 2B.

If f is unknown prior to data collection, a conservative of value of f=0.5 can be used. Under this assumption, the calculated minimum number of barcodes required is 468,750 and the calculated maximum amount of DNA is 1.6 ng, or about 10 million chromatin aggregates.

Samples

The methods described herein are applicable to a number of polynucleotide samples. The polynucleotides consistent with the methods disclosed herein include deoxyribonucleic acids (DNA), ribonucleic acids (RNA) and other forms of nucleic acid. The polynucleotide molecule can be any form of natural, synthetic or modified DNA, including, but not limited to, genomic DNA, complementary DNA, mitochondrial DNA, chloroplast DNA, plasmid DNA, bacterial artificial chromosomes, yeast artificial chromosomes, oligonucleotide tags, recombinant DNA, or combinations thereof. Alternatively, the polynucleotide molecule is any form of natural, synthetic or modified RNA, including, but not limited to mRNA, ribosomal RNA, Xist RNA, and hnRNA. The polynucleotide molecule can be partially or completely in double-stranded or single-stranded form. Samples may comprise DNA generated by primer extension reactions using any suitable combination of primers and a DNA polymerase, including but not limited to polymerase chain reaction (PCR), reverse transcription, and combinations thereof. In cases wherein the template for the primer extension reaction is RNA, the product of reverse transcription can be referred to as complementary DNA (cDNA). Primers useful in primer extension reactions can comprise sequences specific to one or more targets, random sequences, partially random sequences, and combinations thereof. Reaction conditions suitable for primer extension reactions can be determined and optimized. Sample polynucleotides may comprise any polynucleotide present in a sample, which may or may not include target polynucleotides.

The methods described herein are applicable to samples derived from multiple samples of the same individual, samples of different individuals, or combinations thereof. A sample may comprise a plurality of polynucleotides from a single individual. A sample may comprise a plurality of polynucleotides from two or more individuals. A sample can be isolated from various sources, such as a cell sample, tissue sample, or organ sample derived therefrom, including, for example, cultured cell lines, primary cell culture, biopsy, blood sample, tissue explant, organ culture, stool sample, fluid sample or any other tissue or cell preparation, or fraction or derivative thereof or isolated therefrom. A sample can be a primary cell culture or culture adapted cell line including but not limited to genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines, stem cells, germ cells (e.g. sperm, oocytes), transformed cell lines and the like. In some cases, polynucleotide molecules may be obtained from primary cells, cell lines, freshly isolated cells or tissues, frozen cells or tissues, paraffin embedded cells or tissues, fixed cells or tissues, and/or laser dissected cells or tissues. Samples can be obtained from any subject, individual, or biological source including, for example, human or non-human animals, including mammals and non-mammals, vertebrates and invertebrates, and may also be any multicellular organism or single-celled organism such as a eukaryotic or prokaryotic organism, archaeon, microorganisms, and aquatic plankton. In some cases, samples comprise nucleic acids obtained from tumor, cancer, or pre-cancerous cells or tissues. In some cases, samples comprise environmental samples comprising genetic information from more than one organism, such as an organism that is not easily cultured under laboratory conditions. Non-limiting examples of individuals from which a sample or samples may be derived are plants, algae, animals, bacteria, archaea, fungi, protists, monerans, viruses, mitochondria, and chloroplasts. Non-limiting examples of animals are a cow, a pig, a mouse, a rat, a chicken, a cat, a dog, and a mammal, such as a human.

The polynucleotides used in the methods disclosed herein can be of any suitable length. In some cases, polynucleotides used in the methods described herein are at least 100, 200, 300, 400, 500, 750, 1,000, 1,500, 2,000, 2,500, 3,000, 3,500, 4,000, 4,500, 5,000, 6,000, 7,000, 8,000, 9,000, 10,000, 12,000, 14,000, 16,000, 18,000, 20,000 bases or greater than 20,000 bases in length.

Nucleic acid template molecules (e.g., DNA or RNA) can be isolated from a biological sample containing a variety of other components, such as proteins, lipids and non-template nucleic acids. Nucleic acid template molecules can be obtained from any cellular material, obtained from an animal, plant, bacterium, fungus, or any other cellular organism. Biological samples for use in the present disclosure can include viral particles or preparations. Nucleic acid template molecules may be obtained directly from an organism or from a biological sample obtained from an organism, e.g., from blood, urine, cerebrospinal fluid, seminal fluid, saliva, sputum, stool and tissue. Any tissue or body fluid specimen may be used as a source for nucleic acid for use in the disclosure. Nucleic acid template molecules can be isolated from cultured cells, such as a primary cell culture or a cell line. The cells or tissues from which template nucleic acids are obtained may be infected with a virus or other intracellular pathogen. A sample can be total RNA extracted from a biological specimen, a cDNA library, viral, or genomic DNA. A sample can be isolated DNA from a non-cellular origin, e.g. amplified/isolated DNA from the freezer.

Nucleic acids can be extracted and purified using various methods. Nucleic acids can be purified by organic extraction with phenol, phenol/chloroform/isoamyl alcohol, or similar formulations, including TRIzol and TriReagent. Other non-limiting examples of extraction techniques include: (1) organic extraction followed by ethanol precipitation, e.g., using a phenol/chloroform organic reagent (Ausubel et al., 1993), with or without the use of an automated nucleic acid extractor, e.g., the Model 341 DNA Extractor available from Applied Biosystems (Foster City, California); (2) stationary phase adsorption methods (U.S. Pat. No. 5,234,809; Walsh et al., 1991); and (3) salt-induced nucleic acid precipitation methods (Miller et al., 1988), such precipitation methods being typically referred to as "salting-out" methods. Nucleic acid isolation and/or purification may comprise the use of magnetic particles to which nucleic acids can specifically or non-specifically bind, followed by isolation of the beads using a magnet, and washing and eluting the nucleic acids from the beads (see e.g. U.S. Pat. No. 5,705,628). The above isolation methods can be preceded by an enzyme digestion step to help eliminate unwanted protein from the sample, e.g., digestion with proteinase K, or other like proteases. See, e.g., U.S. Pat. No. 7,001,724. If desired, RNase inhibitors may be added to the lysis buffer. For certain cell or sample types, a protein denaturation/digestion step can be added to the protocol. Purification methods may be directed to isolate DNA, RNA, or both. When both DNA and RNA are isolated together during or subsequent to an extraction procedure, further steps may be employed to purify one or both separately from the other. Sub-fractions of extracted nucleic acids can be generated, for example, by purification based on size, sequence, or other physical or chemical characteristic. In addition to an initial nucleic isolation step, purification of nucleic acids can be performed after any step in the methods of the disclosure, such as to remove excess or unwanted reagents, reactants, or products.

Nucleic acid template molecules can be obtained as described in U.S. Patent Application Publication Number US2002/0190663 A1, published Oct. 9, 2003. Nucleic acid molecules can be extracted from a biological sample by a variety of techniques such as those described by Maniatis, et al., Molecular Cloning: A Laboratory Manual, Cold Spring Harbor, New York, pp. 280-281 (1982). The nucleic acids may first be extracted from the biological samples and then cross-linked in vitro. Native association proteins (e.g., histones) can further be removed from the nucleic acids.

The methods disclosed herein can be applied to any high molecular weight double stranded DNA including, for example, DNA isolated from tissues, cell culture, bodily fluids, animal tissue, plant, bacteria, fungi, viruses, etc.

Each of the plurality of independent samples independently may comprise at least 1 ng, 2 ng, 5 ng, 10 ng, 20 ng, 30 ng, 40 ng, 50 ng, 75 ng, 100 ng, 150 ng, 200 ng, 250 ng, 300 ng, 400 ng, 500 ng, 1 µg, 1.5 µg, 2 µg, 5 µg, 10 µg, 20 µg, 50 µg, 100 µg, 200 µg, 500 µg, or 1000 µg, or more of nucleic acid material. In some cases, each of the plurality of independent samples independently may comprise less than about 1 ng, 2 ng, 5 ng, 10 ng, 20 ng, 30 ng, 40 ng, 50 ng, 75 ng, 100 ng, 150 ng, 200 ng, 250 ng, 300 ng, 400 ng, 500 ng, 1 µg, 1.5 µg, 2 µg, 5 µg, 10 µg, 20 µg, 50 µg, 100 µg, 200 µg, 500 µg, 1000 µg or more of nucleic acid.

In some cases, a first nucleic acid segment and a second nucleic acid segment each originate from a first nucleic acid molecule. In some cases, the first nucleic acid segment and the second nucleic acid segment are at least 5, 10, 20, 30, 40, 50, 60, 70, 80, 85, 90, 95, 100, 125, 150, 200, 250, or 300 kb apart on the first nucleic acid molecule. In some cases, at least 0.5%, 0.75%, 1%, 1.25%, 1.5%, 2%, 3%, 4%, 5%, 7.5%, 10%, 12.5%, or 15% of the read-sets comprise a first nucleic acid segment and a second nucleic acid segment that are at least 10 kb apart on the single nucleic acid molecule. In some cases, at least 0.5%, 0.75%, 1%, 1.25%, 1.5%, 2%, 3%, 4%, 5%, 7.5%, 10%, 12.5%, or 15% of the read-sets comprise a first nucleic acid segment and a second nucleic acid segment that are at least 50 kb apart on the single nucleic acid molecule. In some cases, at least 0.5%, 0.75%, 1%, 1.25%, 1.5%, 2%, 3%, 4%, 5%, 7.5%, 10%, 12.5%, or 15% of the read-sets comprise a first nucleic acid segment and a second nucleic acid segment that are at least 25 kb apart on the single nucleic acid molecule. In some cases, at least 0.5%, 0.75%, 1%, 1.25%, 1.5%, 2%, 3%, 4%, 5%, 7.5%, 10%, 12.5%, or 15% of the read-sets comprise a first nucleic acid segment and a second nucleic acid segment that are at least 50 kb apart on the single nucleic acid molecule. In some cases, at least 0.5%, 0.75%, 1%, 1.25%, 1.5%, 2%, 3%, 4%, 5%, 7.5%, 10%, 12.5%, or 15% of the read-sets comprise the first nucleic acid segment and the second nucleic acid segment that are at least 50 kb apart on the single nucleic acid molecule. In some cases, at least 0.5%, 0.75%, 1%, 1.25%, 1.5%, 2%, 3%, 4%, 5%, 7.5%, 10%, 12.5%, or 15% of the read-sets comprise a first nucleic acid segment and a second nucleic acid segment that are at least 75 kb apart on the single nucleic acid molecule. In some cases, at least 0.5%, 0.75%, 1%, 1.25%, 1.5%, 2%, 3%, 4%, 5%, 7.5%, 10%, 12.5%, or 15% of the read-sets comprise a first nucleic acid segment and a second nucleic acid segment that are at least 100 kb apart on the single nucleic acid molecule. In some cases, at least 0.5%, 0.75%, 1%, 1.25%, 1.5%, 2%, 3%, 4%, 5%, 7.5%, 10%, 12.5%, or 15% of the read-sets comprise a first nucleic acid segment and a second nucleic acid segment that are at least 200 kb apart on the single nucleic acid molecule. In some cases, at least 0.5%, 0.75%, 1%, 1.25%, 1.5%, 2%, 3%, 4%, 5%, 7.5%, 10%, 12.5%, or 15% of the read-sets comprise a first nucleic acid segment and a second nucleic acid segment that are at least 300 kb apart on the single nucleic acid molecule.

In many cases, samples comprise multiple copies of each molecule to be phased. Nonetheless, building from individual molecule of origin information, one of skill in the art readily determines phase information with a high degree of confidence.

Phase Data and Uses

In diploid genomes, a haplotype can provide information as to the arrangement of alleles on a chromosome while a genotype can provide information as to alleles at a particular position. A genotype may not define a haplotype. In some cases, it is important to obtain haplotype information and know which allelic variants are physically linked on the same chromosome rather than mapping to the homologous position on a chromosome pair. This process of mapping an allele or other sequence to a specific physical chromosome of a diploid chromosome pair is known as haplotype phasing. Short reads from high-throughput sequence data may not allow the direct observation of allelic variant linkage, for example if the allelic variants are separated by a greater distance than the longest single read. Methods disclosed herein allow for determining the physical linkage of allelic variants using allelic variants on read pairs. Methods described herein may provide for the determination of linked allelic variants based on variant information from labeled sequence segments and/or assembled contigs.

Each individual generally carries two copies of each chromosome, consisting of a long sequence of alleles. The chromosome or set of chromosomes inherited from each parent can be referred to as a haplotype. Genetic variants from each parent can often be inherited together in haplotypes. The determination of haplotype information can generally refer to the genetic variants and variations inherited from one parent.

Haplotype phase information can be used for a variety of applications. Haplotype phase information may be used, for example, to understand the relationship between genetic variation and disease, to detect genotype error, to infer human demographic history, to infer points of recombination, to detect recurrent mutation and signatures of selection, to identify translocations in a nucleic acid sample, and to model cis-regulation of gene expression, or the regulation of transcription by cis-regulatory elements, which are regions non-coding DNA, of nearby genes.

Kits

Disclosed herein are kits comprising one or more components for performing the methods or forming the compositions, in vitro libraries, and phase-tagged nucleic acids described herein. In some cases, a kit comprises at least one of a plurality of association molecules or nucleic acid binding moieties, a cross-linking agent such as a fixative agent, a restriction endonuclease or other enzyme for cleaving, a ligase or other enzyme for attaching oligonucleotides such as barcodes, one or more barcode nucleic acids or adapter oligonucleotides comprising barcodes, or a combination thereof. In some cases, a kit contains one unique barcode sequence. In some cases, the kit contains more than one unique barcode sequence. In some cases, the association molecules are proteins including, but not limited to nucleic acid binding molecules such as histones, transcription factors, and transposases. In some cases, the fixative agent is formaldehyde or any other DNA crosslinking agent.

In some cases, a kit comprises sequencing adapters and/or sequencing primers. In some cases, a kit comprises a device capable of amplifying the read-sets using the sequencing adapters and/or sequencing primers.

In some cases, a kit comprises additional reagents including, but not limited, to lysis buffers, chromatin reconstitution reagents, ligation reagents (e.g. dNTPs, ligase, polynucleotide kinase, and ligase buffer, etc.), and PCR reagents (e.g. dNTPs, polymerase, PCR buffer, and other additives, etc.).

In some cases, a kit includes instructions for using the components of the kit and/or for generating the read-sets.

Computer Systems and Controls

Disclosed herein are simulations that can predict phasing. In some cases, simulation software is used to predict the impact of deviations of various parameters, for example background noise, on phasing inferences. In some cases, the simulations model background noise as a population of barcoded sequence reads that samples the genome independently rather than as part of discrete read sets. Computer systems can be configured and programmed to perform simulations or any of the methods disclosed herein.

Figure 4:
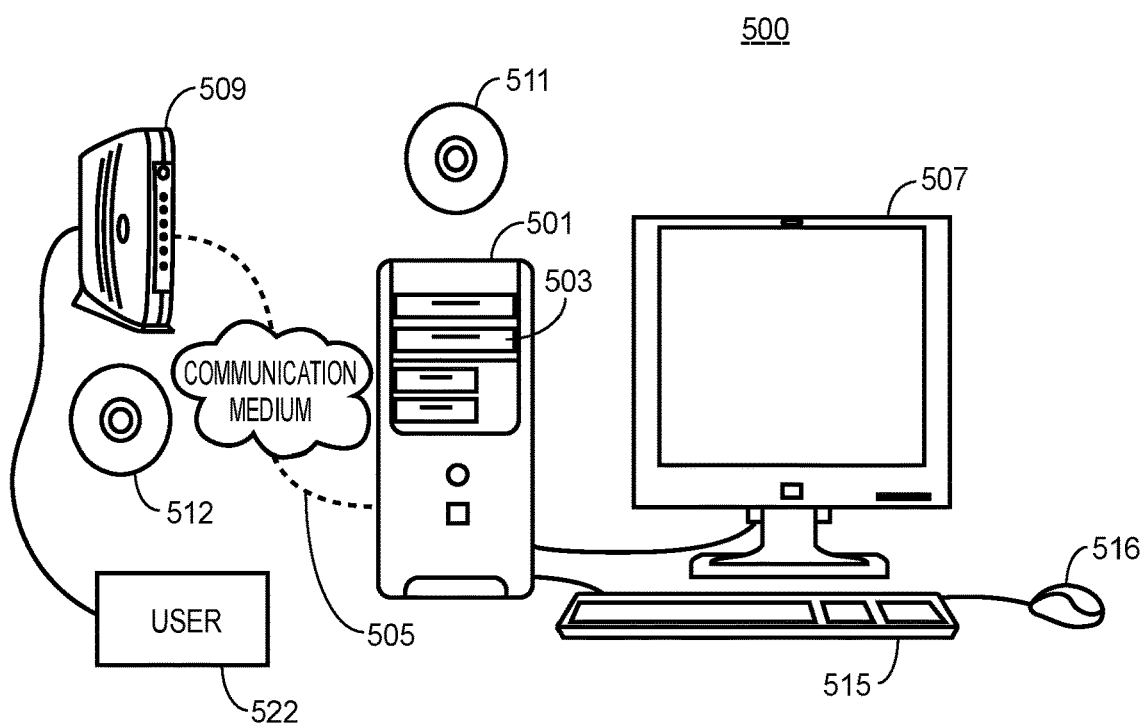
FIG. 4 illustrates various components of an exemplary computer system that can be programmed or configured to implement the methods provided herein.

The computer system 500 illustrated in FIG. 4 may be understood as a logical apparatus that can read instructions from media 511 and/or a network port 505, which is optionally connected to server 509 having fixed media 512. In some cases, the system, such as shown in FIG. 4 includes a CPU 501, disk drives 503, optional input devices such as keyboard 515 and/or mouse 516 and optional monitor 507. In certain cases, data communication is achieved through the indicated communication medium to a server at a local or a remote location. In further cases, the communication medium includes any means of transmitting and/or receiving data. In some cases, the communication medium is a network connection, a wireless connection or an internet connection. In certain examples, such a connection provides for communication over the World Wide Web. It is envisioned that data relating to the present disclosure can be transmitted over such networks or connections for reception and/or review by a party 522 as illustrated in FIG. 4.

Figure 5:
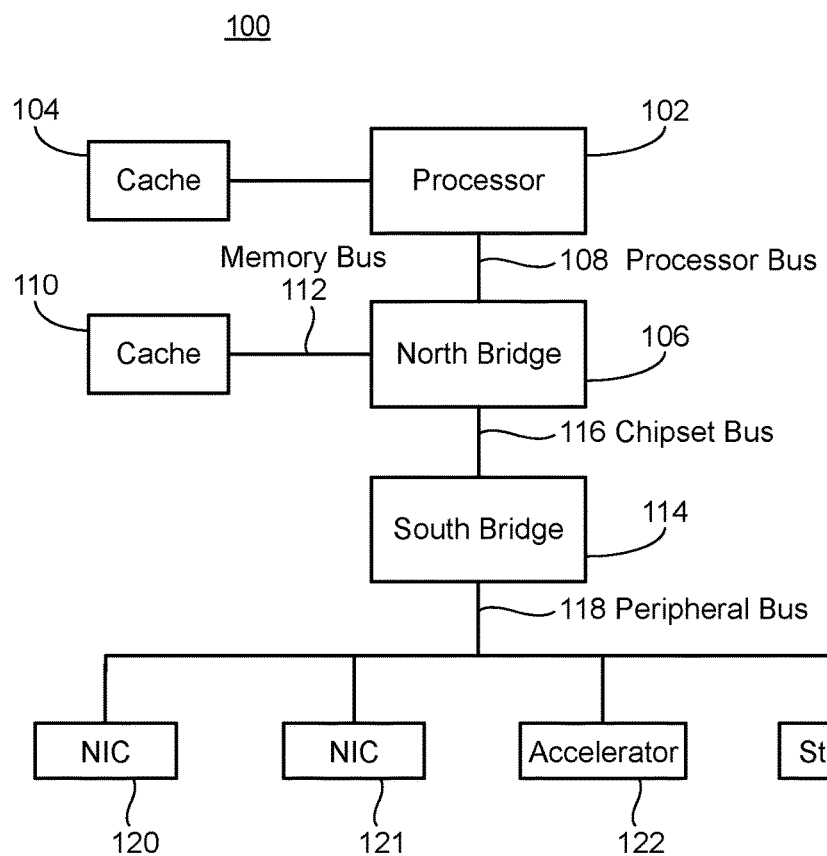
FIG. 5 is a block diagram illustrating the architecture of an exemplary computer system that can be programmed or configured to implement the methods provided herein.

FIG. 5 is a block diagram illustrating a first example architecture of a computer system 100 that can be used in connection with example embodiments of the present disclosure. In certain cases, as depicted in FIG. 5, the example computer system includes a processor 102 for processing instructions. Non-limiting examples of processors include: Intel Xeon™ processor, AMD Opteron™ processor, Samsung 32-bit RISC ARM 1176JZ(F)-S v1.0™ processor, ARM Cortex-A8 Samsung S5PC100™ processor, ARM Cortex-A8 Apple A4™ processor, Marvell PXA 930™ processor, or a functionally-equivalent processor. Multiple threads of execution can be used for parallel processing. In some embodiments, multiple processors or processors with multiple cores are used, whether in a single computer system, in a cluster, or distributed across systems over a network comprising a plurality of computers, cell phones, and/or personal data assistant devices.

In various cases, as illustrated in FIG. 5, a high speed cache 104 is connected to, or incorporated in, the processor 102 to provide a high speed memory for instructions or data that have been recently, or are frequently, used by processor 102. The processor 102 is connected to a north bridge 106 by a processor bus 108. The north bridge 106 is connected to random access memory (RAM) 110 by a memory bus 112 and manages access to the RAM 110 by the processor 102. The north bridge 106 is also connected to a south bridge 114 by a chipset bus 116. The south bridge 114 is, in turn, connected to a peripheral bus 118. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 118. In some alternative architectures, the functionality of the north bridge can be incorporated into the processor instead of using a separate north bridge chip.

In some embodiments, system 100 includes an accelerator card 122 attached to the peripheral bus 118. In some cases, the accelerator includes field programmable gate arrays (FPGAs) or other hardware for accelerating certain processing. In further examples, an accelerator is used for adaptive data restructuring or to evaluate algebraic expressions used in extended set processing.

Software and data are stored in external storage 124 and can be loaded into RAM 110 and/or cache 104 for use by the processor. The system 100 includes an operating system for managing system resources; non-limiting examples of operating systems include: Linux, Windows™, MACOS™, BlackBerry OS™, iOS™, and other functionally-equivalent operating systems, as well as application software running on top of the operating system for managing data storage and optimization in accordance with example embodiments of the present disclosure.

In this example, system 100 also includes network interface cards (NICs) 120 and 121 connected to the peripheral bus for providing network interfaces to external storage, such as Network Attached Storage (NAS) and other computer systems that can be used for distributed parallel processing.

Figure 6:
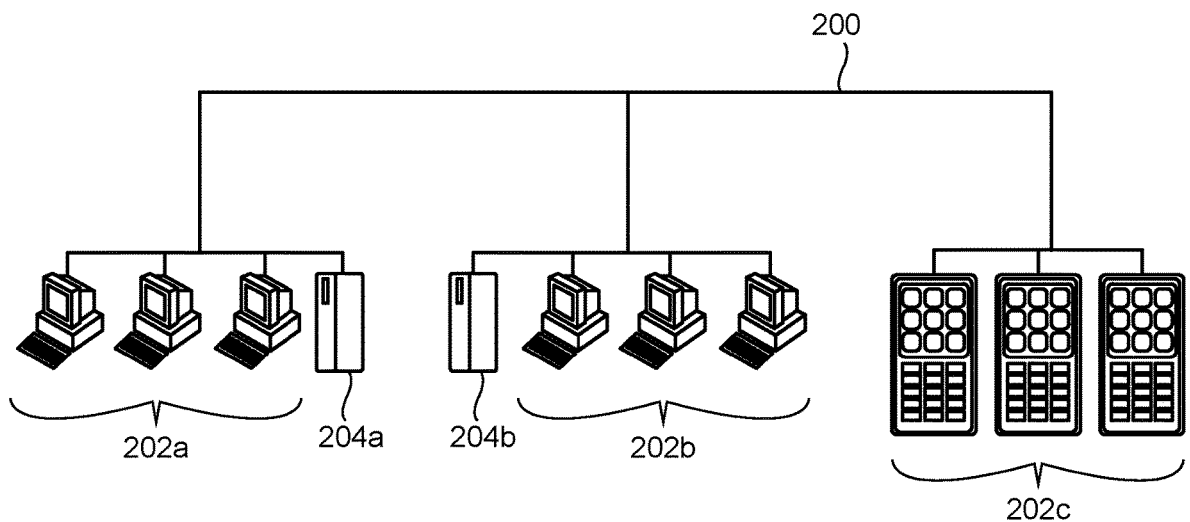
FIG. 6 is a diagram illustrating an exemplary computer network that can be configured to implement the methods provided herein.

FIG. 6 is a diagram showing a network 200 with a plurality of computer systems 202a, and 202b, a plurality of cell phones and personal data assistants 202c, and Network Attached Storage (NAS) 204a, and 204b. In certain examples, systems 202a, 202b, and 202c manage data storage and optimize data access for data stored in Network Attached Storage (NAS) 204a and 204b. In some cases, a mathematical model is used for the data and evaluated using distributed parallel processing across computer systems 202a, and 202b, and cell phone and personal data assistant systems 202c. In certain cases, computer systems 202a, and 202b, and cell phone and personal data assistant systems 202c also provide parallel processing for adaptive data restructuring of the data stored in Network Attached Storage (NAS) 204a and 204b. FIG. 6 illustrates an example only, and a wide variety of other computer architectures and systems are used in conjunction with the various embodiments of the present disclosure. In some cases, a blade server is used to provide parallel processing. In further examples, processor blades are connected through a back plane to provide parallel processing. In certain examples, storage is connected to the back plane or as Network Attached Storage (NAS) through a separate network interface.

In some cases, processors maintain separate memory spaces and transmit data through network interfaces, back plane or other connectors for parallel processing by other processors. In other embodiments, some or all of the processors use a shared virtual address memory space.

Figure 7:
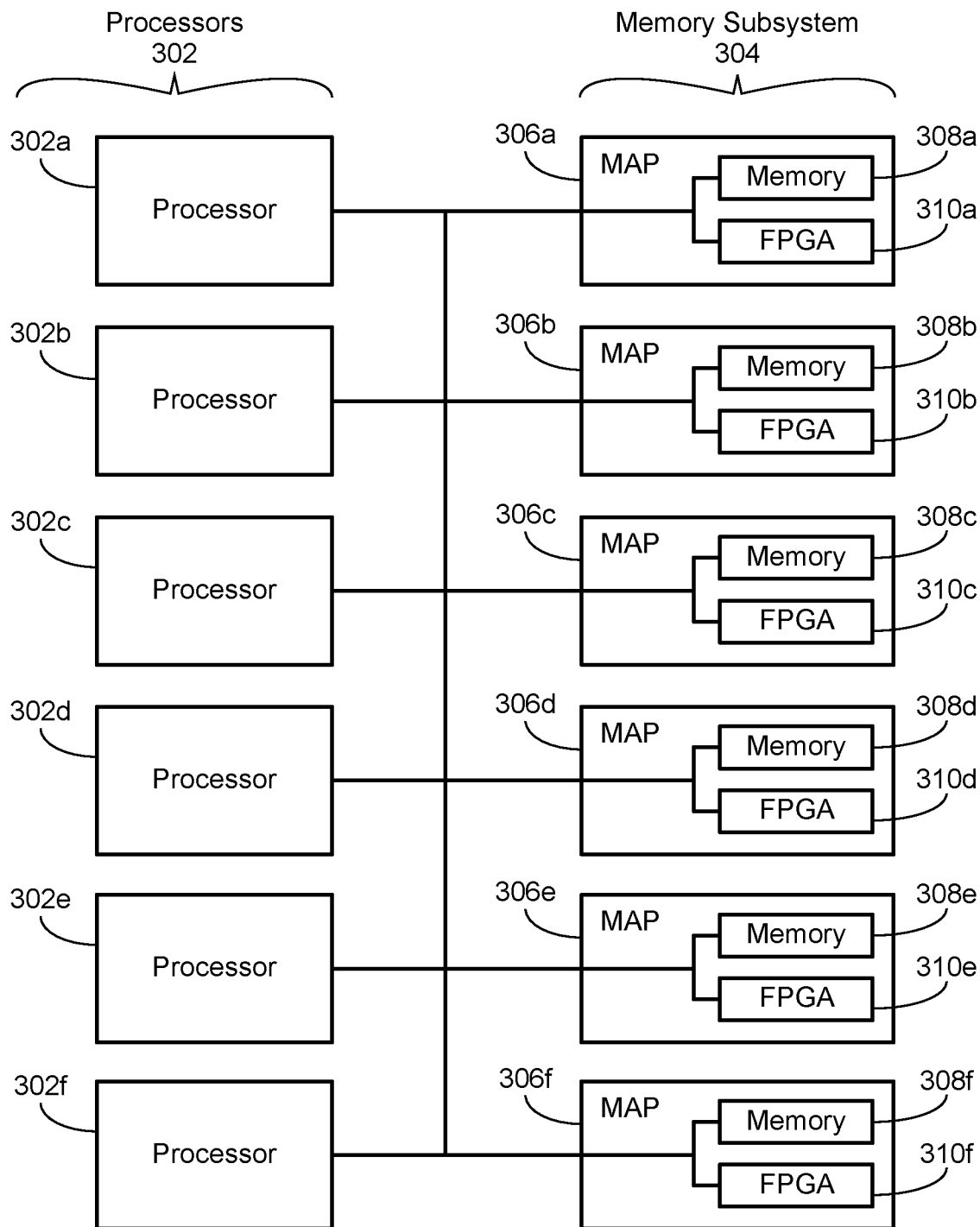
FIG. 7 is a block diagram illustrating the architecture of another exemplary computer system that can be programmed or configured to implement the methods provided herein.

FIG. 7 is a block diagram of a multiprocessor computer system 300 using a shared virtual address memory space in accordance with an example embodiment. The system includes a plurality of processors 302a-f that can access a shared memory subsystem 304. The system incorporates a plurality of programmable hardware memory algorithm processors (MAPs) 306a-f in the memory subsystem 304. In some cases, each MAP 306a-f comprises a memory 308a-f and one or more field programmable gate arrays (FPGAs) 310a-f. The MAP provides a configurable functional unit and particular algorithms or portions of algorithms can be provided to the FPGAs 310a-f for processing in close coordination with a respective processor. In some cases, the MAPs are used to evaluate algebraic expressions regarding the data model and to perform adaptive data restructuring in example embodiments. In this example, each MAP is globally accessible by all of the processors for these purposes. In one configuration, each MAP uses Direct Memory Access (DMA) to access an associated memory 308a-f, allowing it to execute tasks independently of, and asynchronously from, the respective microprocessor 302a-f. In this configuration, a MAP feeds results directly to another MAP for pipelining and parallel execution of algorithms.

The above computer architectures and systems are examples only, and a wide variety of other computer, cell phone, and personal data assistant architectures and systems can be used in connection with exemplary embodiments, including systems using any combination of general processors, co-processors, FPGAs and other programmable logic devices, system on chips (SOCs), application specific integrated circuits (ASICs), and other processing and logic elements. In some embodiments, all or part of the computer system is implemented in software or hardware. In certain cases, any variety of data storage media is used in connection with example embodiments, including random access memory, hard drives, flash memory, tape drives, disk arrays, Network Attached Storage (NAS) and other local or distributed data storage devices and systems.

In some cases, the computer system is implemented using software modules executing on any of the above or other computer architectures and systems. In other embodiments, the functions of the system are implemented partially or completely in firmware, programmable logic devices such as field programmable gate arrays (FPGAs) as referenced in FIG. 7, system on chips (SOCs), application specific integrated circuits (ASICs), or other processing and logic elements. In some cases, the Set Processor and Optimizer is implemented with hardware acceleration through the use of a hardware accelerator card, such as accelerator card 122 illustrated in FIG. 5.

The following examples are intended to illustrate but not limit the disclosure. While they are typical of those that might be used, other procedures known to those skilled in the art may alternatively be used.

EXAMPLES

Example 1. Barcoding Naked DNA

The splitting and pooling scheme for iterative adapter ligation is tested on naked DNA. Three iterations of adapter attachment using three groups, each group containing 8 members, are used. Each member of each group is non-identical to any other member in any other group. With three adapter groups each comprising 8 members each, there are $8^3=512$ possible barcode combinations following iterative attachment. 1-2 ng of naked DNA is first fragmented into multiple segments. Naked DNA can be fragment by any protocol including but not limited to chemical, enzymatic, and mechanical protocols such as sonication, shearing, specific endonuclease treatment, non-specific endonuclease treatment, and enzymatic cleavage. Then, 1 ng of fragmented, naked DNA is split across 8 tubes, each tube containing barcodes having a common barcode sequence that is unique from the other tubes of the first adapter group. Each of the 8 adapters has the same 5' overhang sequence for ligation, but otherwise has a unique dsDNA sequence. The first adapter group is ligated. The naked DNA from the 8 tubes are pooled back together and washed to remove the ligation reaction components. The scheme of distributing into 8 tubes, ligating, and pooling is repeated two additional times with the second and third groups of adapters. Each tube contains barcodes having a barcode sequence that is non-identical to barcode sequences of other tubes. The third adapter group can include a sequence for subsequent enrichment of adapter-ligated DNA during sequencing library preparation through PCR amplification. The library is sequenced, and the sequenced barcode reads can be mapped to the human genome reference sequence. Pairs of reads sharing the same barcode do not provide linkage information, however, since in the fragmentation steps, no binding moiety, such as reconstituted chromatin, is added to ensure that fragments from a common molecule co-segregate through the adapter ligation process. All naked DNA is mixed together, removing information regarding physical linkage.

Example 2. Barcoding with In Vitro Chromatin Aggregates with a Single Iteration

One adapter group containing 8 barcode members is used for a single iteration of adapter attachment. There are $8^1=8$ possible barcodes. Chromatin aggregates are prepared and attached to a solid support of beads. 1 ng of these chromatin aggregates attached to a solid support is split across 8 tubes, each tube containing barcodes of one barcode sequence— that is, each tube contains barcodes that are identical in sequence, and barcodes of two tubes are non-identical in sequence. Each of the 8 adapters has the same 5' overhang sequence for ligation to chromatin aggregates, but otherwise has a unique dsDNA sequence. The adapter group is ligated. The adapter group can include a sequence for subsequent enrichment of adapter-ligated DNA during sequencing library preparation through PCR amplification. The sequencing library is then sequenced. Sequence reads with the same barcode sequence can be clustered together if none of the clusters overlap in nucleic acid sequence.

Example 3. Barcoding with In Vitro Chromatin Aggregates with Two Iterations

Two adapter groups containing 8 barcode members are used for two iterations of adapter attachment. There are $8^2=64$ possible barcode combinations. Chromatin aggregates are prepared and attached to a solid support of beads. 1 ng of chromatin aggregates attached to a solid support of beads is split across 8 tubes containing the barcodes of the first adapter group. Each tube contains one sequence member of an adapter group—that is, each tube contains barcodes that are identical in sequence, and barcodes of two tubes are non-identical in sequence. Each of the 8 adapters has the same 5' overhang sequence for ligation to chromatin aggregates, but otherwise has a unique dsDNA sequence. The first adapter group is ligated. The chromatin aggregates are pooled back together and are washed to remove the ligation reaction components. The scheme of distributing, ligating, and pooling is repeated one additional time with the second group of adapters. The second adapter group can include a sequence for subsequent enrichment of adapter-ligated DNA during sequencing library preparation through PCR amplification. The sequencing library is sequenced. Sequence reads with the same barcode combination can be clustered together provided that clusters do not overlap in sequence. Transposition events may be easier to detect with confidence compared to the use of one adapter group.

Example 4. Barcoding with In Vitro Chromatin Aggregates with Three Iterations

Cross-linked chromatin aggregates are tagged by iterative adapter attachment using three groups of double-stranded DNA (dsDNA) adapters using the splitting and pooling scheme depicted in FIG. 1A. There are 8 members of each adapter group, each of which contains a unique barcode sequence. The number of barcode combinations is $8^3=512$. Chromatin aggregates are prepared and attached to a solid support of beads. 1 ng of chromatin aggregates attached to a solid support of beads is split across 8 tubes containing the barcodes of the first adapter group, each tube contains barcodes of one sequence member of the first adapter group. That is, each tube contains barcodes having identical sequences but between two tubes, the barcode sequences are non-identical. These adapters are ligated to the chromatin aggregates. Then, the chromatin aggregates are pooled and mixed, and the ligation reaction components can be removed. This scheme of distributing into 8 aliquots, ligating, and pooling is repeated two additional times with the remaining second and third adapter groups. Similarly, each tube contains barcodes having one sequence member of the second adapter group or third adapter group and each sequence member is non-identical to another sequence member. The third adapter group can include a sequence for subsequent enrichment of adapter-ligated DNA during sequencing library preparation through PCR amplification. The library is sequenced and 4.7 million sequenced barcoded reads can be mapped with high confidence to the human genome reference sequence.

The presence of multiple reads from individual chromatin aggregates is tested by comparing the distribution of distances along the genome between successive reads bearing the same barcode to the distribution after computational randomization of the read-barcode associations. Results from simulations using parameters chosen to match the characteristics of this example (e.g., simulated 70% of noise reads) and analyzed similarly to results of the example are in agreement with results of the example. Analysis of sequencing data shows that the majority (331) of the 512 barcodes are represented within a factor of 2 of the expected number of reads per barcode. Although this example is performed with sub-optimal parameters (e.g., limited number of sequence reads and small number of barcode permutations), a statistically significant excess of pairs of reads that share the same barcode and are separated by a distance that is within the size of the input DNA is observed as shown in FIG. 3. Simulation results demonstrates that haplotype phasing can be achieved by tagging DNA molecules with barcodes that can be grouped after sequencing to reconstruct these molecules, even in the presence of substantial noise.

There can be any number, N, of members in an adapter group and any number, M, of iterations of adapter attachment. This can result in NM number of barcode combinations. A larger number N may result in a smaller percentage of chromatin aggregates having the same barcode and/or barcode combination. This method can be scaled to adapter sets containing more than 8 members, e.g., 96 members per adapter group.

Example 5. Barcoding with In Vitro Chromatin Aggregates with 96 Barcodes and Three Iterations The splitting and pooling scheme of FIG. 1A is increased in scale with in vitro chromatin aggregates. Three adapter groups containing 96 members each are tested. Each sequence member is non-identical to any other sequence member. The possible number of barcode permutations is 96³=884,736. This 96³ can be processed in a resource-efficient manner with, e.g., 96-well plates, a multichannel pipettor, and plastic basins designed for use with such a pipettor. Chromatin aggregates are prepared and attached to a solid support of beads. 1 ng of these chromatin aggregates attached to beads is split across 96 wells containing the members of the first adapter group to be ligated. Each of the 96 adapters has the same 5' overhang sequence for ligation to chromatin aggregates, but otherwise has a unique dsDNA sequence. The first adapter group is ligated. The chromatin aggregates are pooled back together and are washed to remove the ligation reaction components. The scheme of distributing, ligating, and pooling is repeated two additional times with the second and third groups of adapters, each containing 96 members. The third adapter group can include a sequence for subsequent enrichment of adapter-ligated DNA during sequencing library preparation through PCR amplification. Sequencing reads are obtained for at least 150 nucleotides, and approximately the first 50 nucleotides comprise a barcode sequence, while the remaining nucleotides represent genomic sequences.

Example 6. MboI Digestion of Cross-Linked Chromatin Aggregates

Cross-linked chromatin aggregates are prepared by digestion with the restriction enzyme MboI, which produces 5'-GATC overhangs. These overhangs are partially filled in with dideoxy-dGTP and create non-palindromic 5'-GAT overhangs. To test ligation efficiency, three 12 bp dsDNA adapters comprising barcodes with a Tm of about 40° C. and appropriate 3-nucleotide 5' overhangs are sequentially ligated to chromatin aggregates, and a sequencing library is prepared from the DNA. The resulting sequencing data is analyzed to determine 1) the efficiency of ligating chromatin aggregates to the first adapter; and 2) the efficiency of the subsequent, sequential adapter ligations. Sequencing data indicates that the first adapter is ligated to free nucleic acid ends of the chromatin aggregates at an efficiency of 80%, the second adapter is ligated at an efficiency of 75%, and the third adapter is ligated at an efficiency of 90%. The resulting efficiency of all ligation steps in series is 54%.

Example 7. Evaluating Parameters for Haplotype Phasing of the Human Genome

Sequencing data is analyzed to determine if sequencing reads can be grouped into read sets with an average of 10 reads per set. Results are used to determine f and re-calculate the minimum number of barcodes for haplotype phasing. For example, if f is observed to be 0.2, the amount of DNA to sample can be increased. The number of barcode permutations can also be increased if clustering is not observed initially.

Example 8. Packaging a Nucleic Acid Sample into Phase-Tagged Fragments

A nucleic acid sample is packaged into phase-tagged fragments. First, intramolecular phosphodiester backbone-independent bonds are formed to cross-link each constituent of the nucleic acid sample to association molecules such as histones to form nucleic acid complexes. Each complex comprises a single constituent of the nucleic acid sample. Next, each constituent of the nucleic acid sample is cleaved to expose at least one pair of internal double-strand break ends. Then, each constituent of the nucleic acid sample is tagged at the at least one pair of internal double-strand break ends with a first tag set comprising a barcode. Each constituent of the nucleic acid sample is tagged at the at least one pair of internal double-strand break ends with a second tag set comprising a barcode. Each constituent of the nucleic acid sample is then tagged at the at least one pair of internal double-strand break ends with a third tag set comprising a barcode. The presence of a non-identical first tag set, second tag set, and third tag set on a pair of molecules indicates that the pair of molecules originates from non-identical constituents of the nucleic acid sample.

Example 9. Forming Nucleic Acid Compositions from an Organism

A nucleic acid composition from an organism comprising a nucleic acid library is formed. A plurality of nucleic acids from an organism is cross-linked, for example to in vitro assembled chromatin to form chromatin aggregates. The plurality of nucleic acids cross-linked to in vitro assembled chromatin is digested by an endonuclease, for example MboI. The cross-linked nucleic acids are iteratively labeled with a first tag, a second tag, and a third tag, each of which are 9 bases in length. The labeled nucleic acids are then sequenced to form a nucleic acid library. Each library constituent comprises a nucleic acid comprising a nucleic acid sample segment, a first tag, a second tag, and a third tag. A different between a first library constituent and a second library constituent in any one of a first tag sequence, second tag sequence, and third tag sequence indicates that the first library constituent and the second library constituent do not originate from a common nucleic acid molecule.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of generating a first read-set and a second read-set from a biological sample comprising a first nucleic acid molecule and a second nucleic acid molecule, comprising:
   (a) obtaining a first complex comprising a first nucleic acid molecule bound to a first polypeptide and a second complex comprising a second nucleic acid molecule bound to a second polypeptide, wherein said first nucleic acid molecule comprises a first nucleic acid segment and a second nucleic acid segment, and wherein said second nucleic acid molecule comprises a third nucleic acid segment and a fourth nucleic acid segment;
   (b) creating a first multi-labeled complex and a second multi-labeled complex by subjecting said first complex and said second complex to multiple rounds of labeling, each round of labeling comprising:
      (i) separating said first complex from said second complex;
      (ii) labelling said first nucleic acid segment and said second nucleic acid segment using a first random barcode nucleic acid, thereby creating a first labeled complex;
      (iii) labeling said third nucleic acid segment and said fourth nucleic acid segment using a second random barcode nucleic acid, thereby creating a second labeled complex;
      (iv) pooling said first labeled complex and said second labeled complex;
   (c) sequencing said first nucleic acid segment and said second nucleic acid segment of said first multi-labeled complex, thereby obtaining said first read-set;
   (d) sequencing said third nucleic acid segment and said fourth nucleic acid segment of said second multi-labeled complex, thereby obtaining said second read-set; and
   (e) assigning sequence from said third nucleic acid segment and said first nucleic acid segment to separate molecules because said sequences from said first nucleic acid segment and said third nucleic acid segment comprise non-identical barcode ends.

2. The method of claim 1, wherein (b) is repeated at least three times to create a triply labeled first complex and a triply labeled second complex.

3. The method of claim 1, wherein (i) said first nucleic acid segment and said second nucleic acid segment, and (ii) said third nucleic acid segment and said fourth nucleic acid segment are treated so as to not share a common phosphodiester backbone.

4. The method of claim 3, wherein (i) said first nucleic acid segment and said second nucleic acid segment, and (ii) said third nucleic acid segment and said fourth nucleic acid segment are treated with an enzyme so as to not share a common phosphodiester backbone.

5. The method of claim 4, wherein said enzyme is a non-specific endonuclease, a specific endonuclease, or a transposase.

6. The method of claim 3, wherein (i) said first nucleic acid segment and said second nucleic acid segment, and (ii) said third nucleic acid segment and said fourth nucleic acid segment are sonicated or sheared so as to not share a common phosphodiester backbone.

7. The method of claim 1, wherein said first polypeptide is crosslinked to said first nucleic acid molecule.

8. The method of claim 7, wherein said first polypeptide is crosslinked to said first nucleic acid molecule with formaldehyde, psoralen, or UV light.

9. The method of claim 7, wherein said second polypeptide is crosslinked to said second nucleic acid molecule.

10. The method of claim 9, wherein said second polypeptide is crosslinked to said second nucleic acid molecule with formaldehyde, psoralen, or UV light.

11. The method of 1, wherein said first read-set is generated by associating sequence from said first nucleic acid segment and said second nucleic acid segment using a sequence of said first random barcode nucleic acid.

12. The method of 1, wherein said second read-set is generated by associating sequence from said third nucleic acid segment and said fourth nucleic acid segment using a sequence of said second random barcode nucleic acid.

13. The method of claim 1, comprising assembling a first contig having sequence from said first nucleic acid segment and a second contig having sequence from said second nucleic acid segment into a first scaffold.

14. The method of claim 1, comprising assembling a second contig having sequence from said third nucleic acid segment and a fourth contig having sequence from said fourth nucleic acid segment into a second scaffold.

15. The method of claim 1, comprising assigning sequence from said first nucleic acid segment and said second nucleic acid segment to a first common phase.

16. The method of claim 1, comprising assigning sequence from said third nucleic acid segment and said fourth nucleic acid segment to a second common phase.

17. The method of claim 1, wherein said first read-set and said second read-set are used to determine phase of said first nucleic acid molecule and said second nucleic acid molecule.

18. The method of claim 1, wherein said first random barcode and said second random barcode are randomly selected from a plurality of unique barcodes.

19. The method of claim 1, wherein said polypeptide comprises a histone.

20. The method of claim 1, wherein said biological sample is derived from an organism selected from a plant, an algae, an animal, a bacterium, an archaea, a fungus, a protist, a moneran, a virus, or a combination thereof.

* * * * *